(12) United States Patent
Jeong

(10) Patent No.: US 9,120,760 B2
(45) Date of Patent: Sep. 1, 2015

(54) FLUORO-HOMONEPLANOCIN A AND NUCLEOSIDE DERIVATIVES, METHOD FOR THE SYNTHESIS THEREOF, AND THE PHARMACEUTICAL COMPOSITIONS COMPRISING THE SAME AS AN ACTIVE COMPONENT FOR TREATMENT OF CANCER

(71) Applicant: EWHA UNIVERSITY—INDUSTRY COLLABORATION FOUNDATION, Seoul (KR)

(72) Inventor: Lak Shin Jeong, Seoul (KR)

(73) Assignee: EWHA University—Industry Collaboration Foundation, Seoul (KR)

( * ) Notice: Subject to any disclaimer, the term of this patent is extended or adjusted under 35 U.S.C. 154(b) by 65 days.

(21) Appl. No.: 13/861,089

(22) Filed: Apr. 11, 2013

(65) Prior Publication Data

US 2013/0310403 A1 Nov. 21, 2013

(30) Foreign Application Priority Data

May 15, 2012 (KR) ......................... 10-2012-0051714

(51) Int. Cl.
| | | |
|---|---|---|
| *C07D 473/34* | (2006.01) | |
| *A61K 31/52* | (2006.01) | |
| *C07D 239/22* | (2006.01) | |
| *C07D 473/00* | (2006.01) | |
| *C07D 239/54* | (2006.01) | |

(52) U.S. Cl.
CPC .............. *C07D 239/22* (2013.01); *A61K 31/52* (2013.01); *C07D 239/54* (2013.01); *C07D 473/00* (2013.01); *C07D 473/34* (2013.01)

(58) Field of Classification Search
CPC ..................................................... C07D 473/34
See application file for complete search history.

(56) References Cited

PUBLICATIONS

Choi, WJ et al. Fluorocyclopentenyl-cytosine with Broad Spectrum and Potent Antitumor Activity, J. Med. Chem. 2012, vol. 55: pp. 4521-4525; entire document.
Chandra, et al., Stereoselective Snythesis of Fluoro-homoneplanocin A as a Potential Antiviral Agent, Mar. 16, 2012, pp. 2134-2137, vol. 14, No. 8, Organic Letters.
Turner, M. A.; Yang, X.; Yin, D.; Kuczera, K.; Borchardt, R. T.; Howell, P. L. Structure and function of S-adenosylhomocysteine hydrolase. Cell biochemistry andbiophysics2000, 33, 101-125.
Cantoni, G. L. The centrality of S-adenosylhomocysteinase in the regulation of the biological utilization of Sadenosylmethionine. In Biological methylation and drug design, Borchardt, R. T.; Creveling, C. R.; Ueland, P. M., Eds. Humana Press: Clifton, N.J., 1986; pp. 227-238.
Wolfe, M. S.; Borchardt, R. T. J. Med. Chem. 1991, 34, 1521-1530.
Keller, B. T.; Borchardt, R. T. Metabolism and mechanism of action of neplanocin A-A potent inhibitor of Sadenosylhomocysteine hydrolase. In Biological methylation and drug design, Borchardt, R. T.; Creveling, C. R.; Ueland, P. M., Eds. Humana Press: Clifton, N.J.,1986; pp. 385-396.
Shuto,S.; Obara, T.; Saito,Y.; Andrei, G.; Snoeck, R.; De Clercq, E.; Matsuda, A. J. Med. Chem. 1996, 39, 2392-2399.
Yang, M.; Schneller, S. W.; Korba, B. J. Med. Chem. 2005, 48, 5043-5046.
Lee, K. M.; Choi, W. J.; Lee, Y. et al., J. Med. Chem. 2011, 54, 930-938.
Jeong, L. S.; Yoo, S. J. et al., Med. Chem. 2003, 46, 201-203.

*Primary Examiner* — James D Anderson
(74) *Attorney, Agent, or Firm* — Benjamin Aaron Adler

(57) ABSTRACT

The present invention relates to a fluoro-homoneplanocin A, its nucleoside derivative, and synthetic methods. The novel fluoro-homoneplanocin A and its nucleoside derivative in the present invention have an effect on cancer prevention or treatment, and therefore can be used as anticancer drugs.

3 Claims, 9 Drawing Sheets

Scheme I

Scheme II

Scheme III       FIG. 3

Scheme IV

Scheme V

X is Cl, Br, or I,
$R_1$ is $NH_2$ or $NH(CH_3)$,
$R_2$ is H, Cl, Br, or $NH_2$

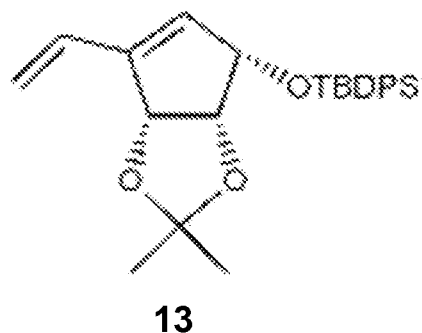
13
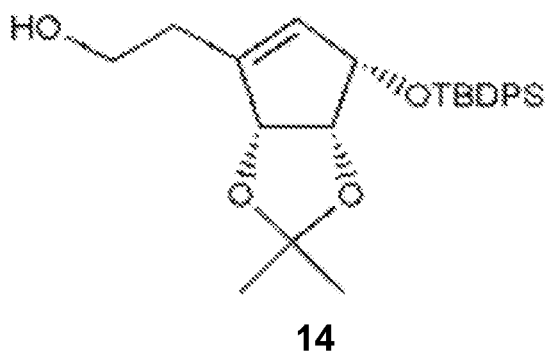
14
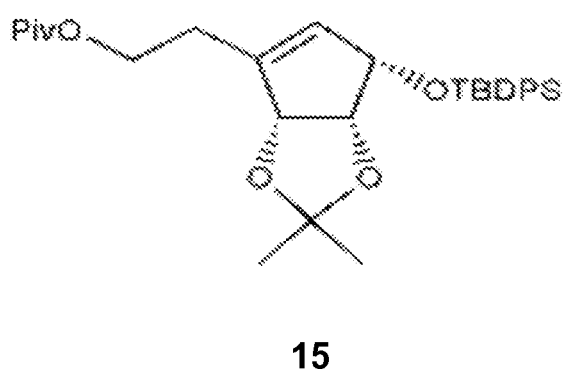
15
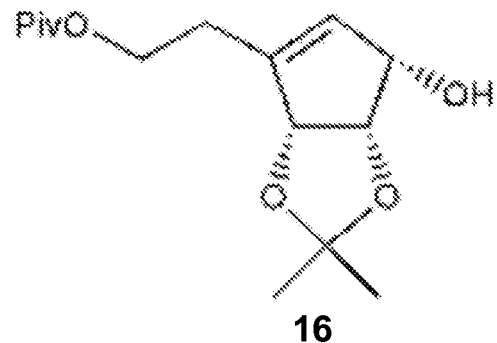
16
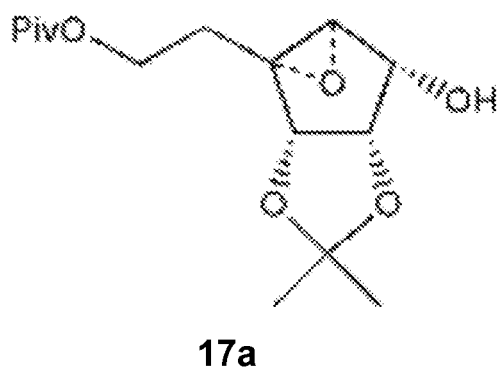
17a
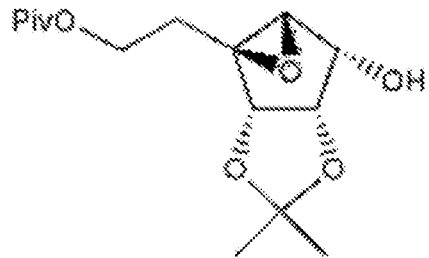
17b
FIG. 6C

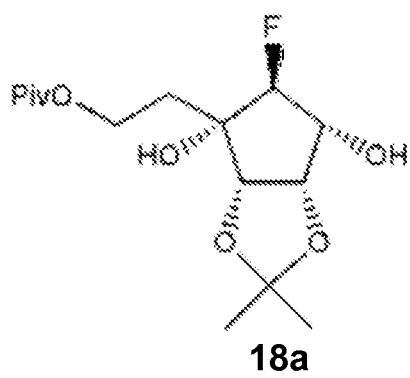
18a
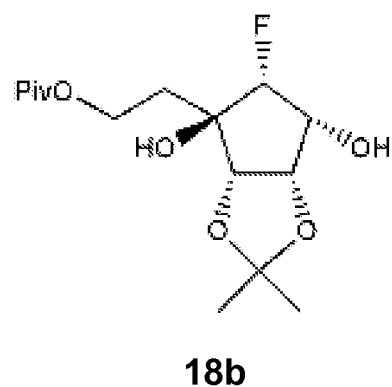
18b
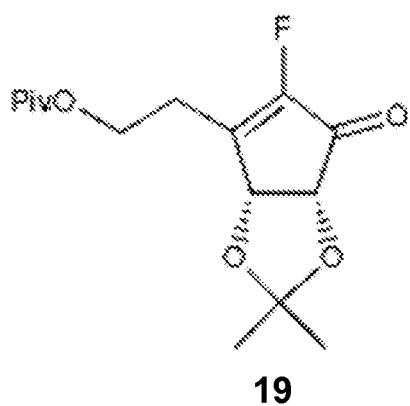
19
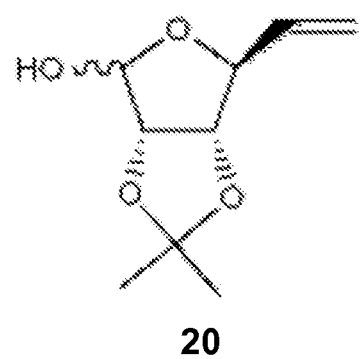
20
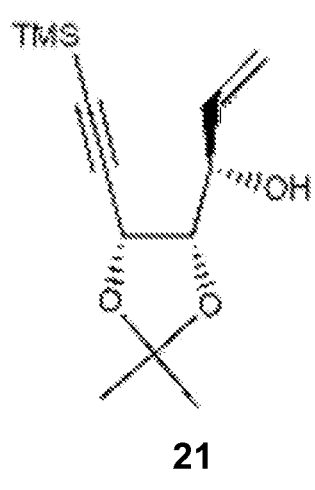
21
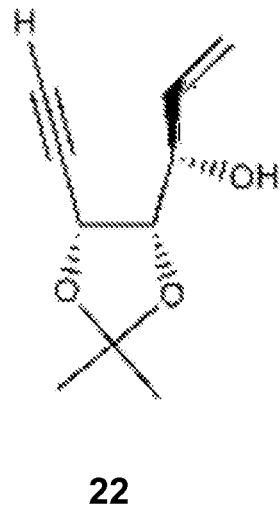
22
FIG. 6D

FLUORO-HOMONEPLANOCIN A AND NUCLEOSIDE DERIVATIVES, METHOD FOR THE SYNTHESIS THEREOF, AND THE PHARMACEUTICAL COMPOSITIONS COMPRISING THE SAME AS AN ACTIVE COMPONENT FOR TREATMENT OF CANCER

TECHNICAL FIELD

The present invention relates to a novel fluoro-homoneplanocin A, nucleoside derivative thereof, and preparation methods of the same. The present invention also relates to a pharmacological composition comprising a novel fluoro-homoneplanocin A and nucleoside derivative thereof for prevention or treatment of cancer.

BACKGROUND ART

Neplanocin A, which is isolated from *Aspergillus niger*, is the carbocyclic nucleoside which inhibits S-adenosylhomocystein hydrolase (SAH). SAH hydrolase is an enzyme that catalyzes the hydrolysis of S-adenosylhomocystein into adenosine and L-homocystein, and it has been reported that S-adenosylhomocystein is accumulated in the cell and exhibits antiviral activity by inhibiting S-adenosyl-L-methionine (SAM) dependent methyltransferase which is crucial for methylation in the cell as a feedback when SHA hydrolase is inhibited. (Turner et al., *Cell Biochemistry and Biophysics* 2000, 33, 101-125. Cantoni, G. L., In *Biological Methylation and Drug Design.*, Borchardt, R. T., Creveling, C. R., Ueland, P. M., Eds. Humana Press: Clifton, N.J., 1986; pp 227-238; and Wolfe, M. S and Borchardt, R. T. *J. Med. Chem.* 1991, 34, 1521-1530 and the proofs cited in the above references).

Therefore, many compounds for inhibiting SAH hydrolase have been synthesized and neplanocin A, among them, has been reported to exhibit the potent anticancer and antiviral activity. Fluoro-neplanocin A has been synthesized based on the structure of neplanocin A and reported to exhibit the potent antivirus activity (Keller et al. In *Biological Methylation and Drug Design.*, Borchardt, R. T., Creveling, C. R., Ueland, P. M., Eds. Humana Press: Clifton, N.J., 1986; pp 385-396).

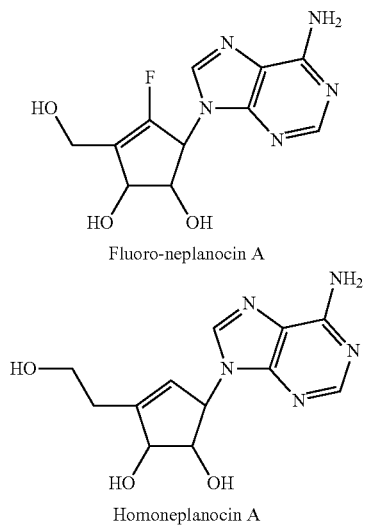

Fluoro-neplanocin A

Homoneplanocin A

Meanwhile, homoneplanocin A, derived from neplanocin A by adding one carbon, has also been reported to exhibit the potent inhibitive activity against SAH hydrolase (Shuto et al. Med. Chem. 1996, 39, 2392-2399)and the potent activity against hepatitis B virus. (Yang, M.; Schneller, S. W.; Korba, B. J. Med. Chem. 2005, 48, 5043-5046). Researchers have tried to synthesize fluoro-homoneplanocin A by combining fluoro-neplanocin A with homo-neplanocin A, using a conventional method. However, since it was difficult to prepare a derivate with one additional carbon using the conventional methods, fluoro-homoneplanocin A could not be prepared.

Accordingly, the present inventors have identified that the fluoro-homoneplanocin A can be synthesized by using (1S, 4R,5S)-3-Ethenyl-4,5-(O-isopropylidenedioxy)-4-cyclopent-2(3)-en-1-ol as a starting substance, which can be synthesized by using D-ribose, also as a starting substance, through enynering-closing metathesis. (Jeong et al., Med. Chem. 2003, 46, 201-203. Lee et al., Med. Chem. 2011, 54, 930-938). Also they identified that the uracil- or cytosine-substituted nucleoside derivative can be synthesized using the above compounds as starting substances. The present inventors completed the present invention by identifying that the fluoro-homoneplanocin A with the novel structure obtained by the above synthesis has an inhibitory effect against cancer cells as an anticancer drug.

SUMMARY OF THE INVENTION

Generally, the technical problem to solve is to provide a novel fluoro-homoneplanocin A and nucleoside derivatives thereof as well as the synthetic methods for the same. Also, it is desired to provide pharmaceutical compositions of the new fluoro-homoneplanocin A and nucleoside derivatives thereof for the prevention or treatment of cancer. The present invention provides the compound represented by Formula 1 or 2, or the pharmacologically acceptable salts thereof and pharmaceutical compositions as shown below:

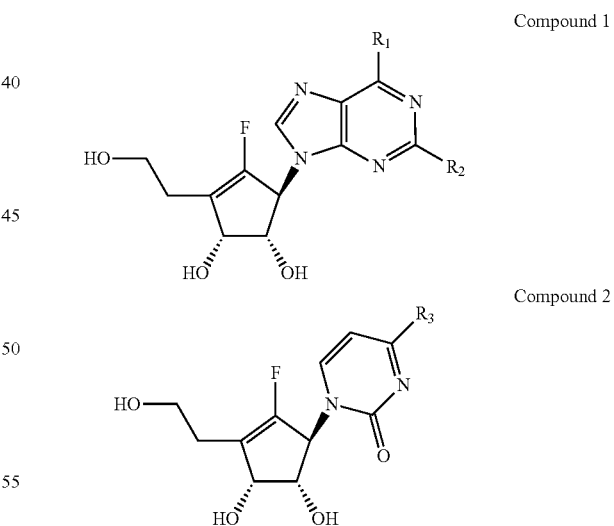

Compound 1

Compound 2 wherein $R_1$ is $NH_2$ or $NH(CH_3)$, $R_2$ is H, Cl, Br, or $NH_2$, $R_3$ is OH or $NH_2$. The methods for preparing compounds encompassed by these structural formulas is well-described in the Examples.

BRIEF DESCRIPTION OF THE DRAWINGS

FIGS. 6A-6D depict chemical structural formulas 1-22 of the compounds, intermediates and products in chemical schemes I-V.

DETAILED DESCRIPTION OF THE INVENTION

Provided herein are novel fluoro-homoneplanocin A and nucleoside derivatives thereof and their pharmacologically acceptable salts and pharmaceutical compositions thereof. These compounds are useful for the prevention or treatment of cancer. The present invention provides the compound represented by Formula 1 or 2, or the pharmacologically acceptable salts thereof, as shown below:

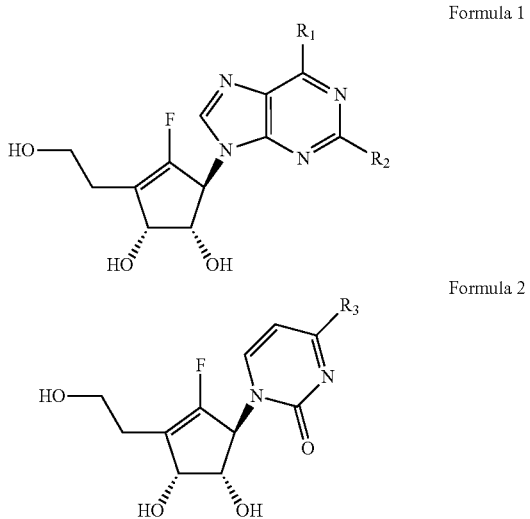

wherein $R_1$ is $NH_2$ or $NH(CH_3)$, $R_2$ is H, Cl, Br, or $NH_2$, $R_3$ is OH or $NH_2$. The $R_1$ is preferably $NH_2$, $R_2$ is preferably H, and $R_3$ is preferably OH or $NH_2$.

Figure 3:
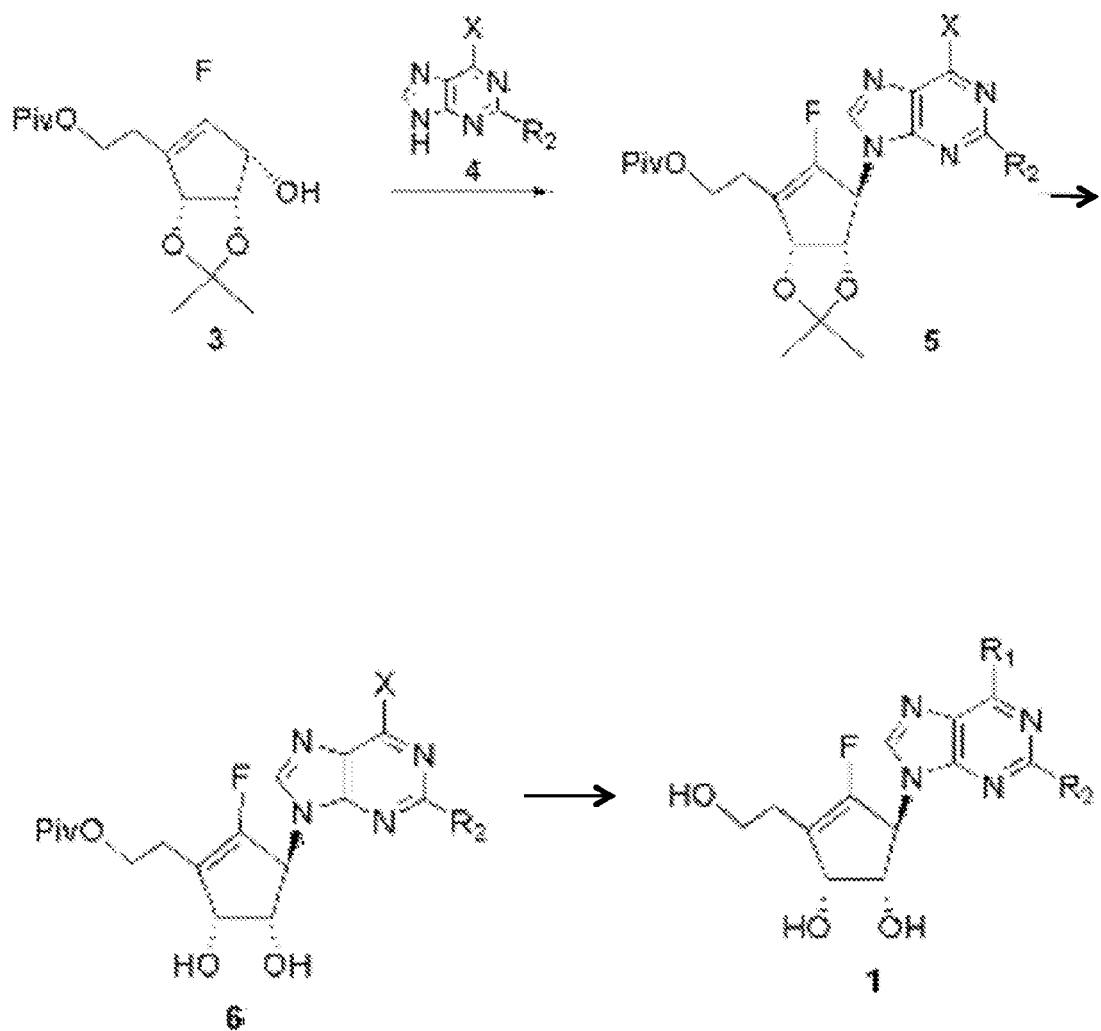
FIG. 3 is chemical scheme III for the synthesis of (1S,2R,5S)-5-(6-Aminopurine-9-yl)-4-fluoro-3-hydroxyethyl-cyclopent-3(4)-en-1,2-diol (Formula 1; X is $NH_2$, $R_2$ is H).

Also, the present invention provides methods for synthesizing or preparing a compound of Formula 1. The method steps comprise preparing 2,2-Dimethyl-propionic acid 2-[(2R,3S,4S)-4-(6-chloro-purine-9-yl)-5-fluoro-2, 3-(O-(O-Isopropylidenedioxy))-1(5)-en]-ethyl ester (Compound 5) by reacting 2,2-Dimethyl-propionic acid2-[(3S,4R,5S)-2-fluoro-4,5-(O-isopropylidenedioxy)-3-ol-cyclopent-1(2)-en]-ethyl ester (Compound 3) with 6-chloro-purine (Compound 4); preparing 2,2-Dimethyl-propionic acid 2-[(2R,3S,4S)-4-(6-chloro-purine-9-yl)-5-fluoro-2,3-dihydroxycyclopent-1(5)-en]-ethyl ester (Compound 6) by reacting 2-[(2R,3S,4S)-4-(6-chloro-purine-9-yl)-5-fluoro-2,3-(O-(O-Isopropylidenedioxy))-1(5)-en]-ethyl ester (Compound 5) with an acid; and preparing the compound of Formula 1 by reacting 2,2-Dimethyl-propionic acid 2-[(2R,3S, 4S)-4-(6-chloro-purine-9-yl)-5-fluoro-2,3-dihydroxy cyclopent-1(5)-en]-ethyl ester (Compound 6) with $NH_3$ or $NH_2(CH_3)$ followed by removing the protecting group. The Formula 1 compounds may be (1S,2R,5S)-5-(6-Amino purine-9-yl)-4-fluoro-3-hydroxyethyl-cyclopent-3(4)-en-1, 2-diol or (1S,2R,5S)-5-(6-Methylamino purine-9-yl)-4-fluoro-3-hydroxyethyl-cyclopent-3(4)-en-1,2-diol. The preparation method according to the present invention is schematically shown in FIG. 3.

The 2,2-Dimethyl-propionic acid 2-[(2R,3S,4S)-4-(6-chloro-purine-9-yl)-5-fluoro-2,3-(O-(O-Isopropylidenedioxy))-1(5)-en]ethyl ester (Compound 5) is synthesized by condensing 2,2-Dimethyl-propionic acid 2-[(3S,4R,5S)-2-fluoro-4,5-(O-isopropylidenedioxy)-3-ol cyclopent-1(2)-en]-ethyl ester (Compound 3), which provides a glycosyl group, with 6-chloro-purine (Compound 4 or a purine derivative) under Mitsunobu conditions. The resultant compound of 2,2-Dimethyl-propionic acid 2-[(2R,3S,4S)-4-(6-chloro-purine-9-yl)-5-fluoro-2,3-dihydroxycyclopent-1(5)-en]-ethyl ester (Compound 6) is processed with ammonia or $NH_2(CH_3)$, then processed further with NaOMe, producing fluoro-homoneplanocin A, the final compound, and derivatives thereof, such as, compounds of Formula 1.

Figure 4:
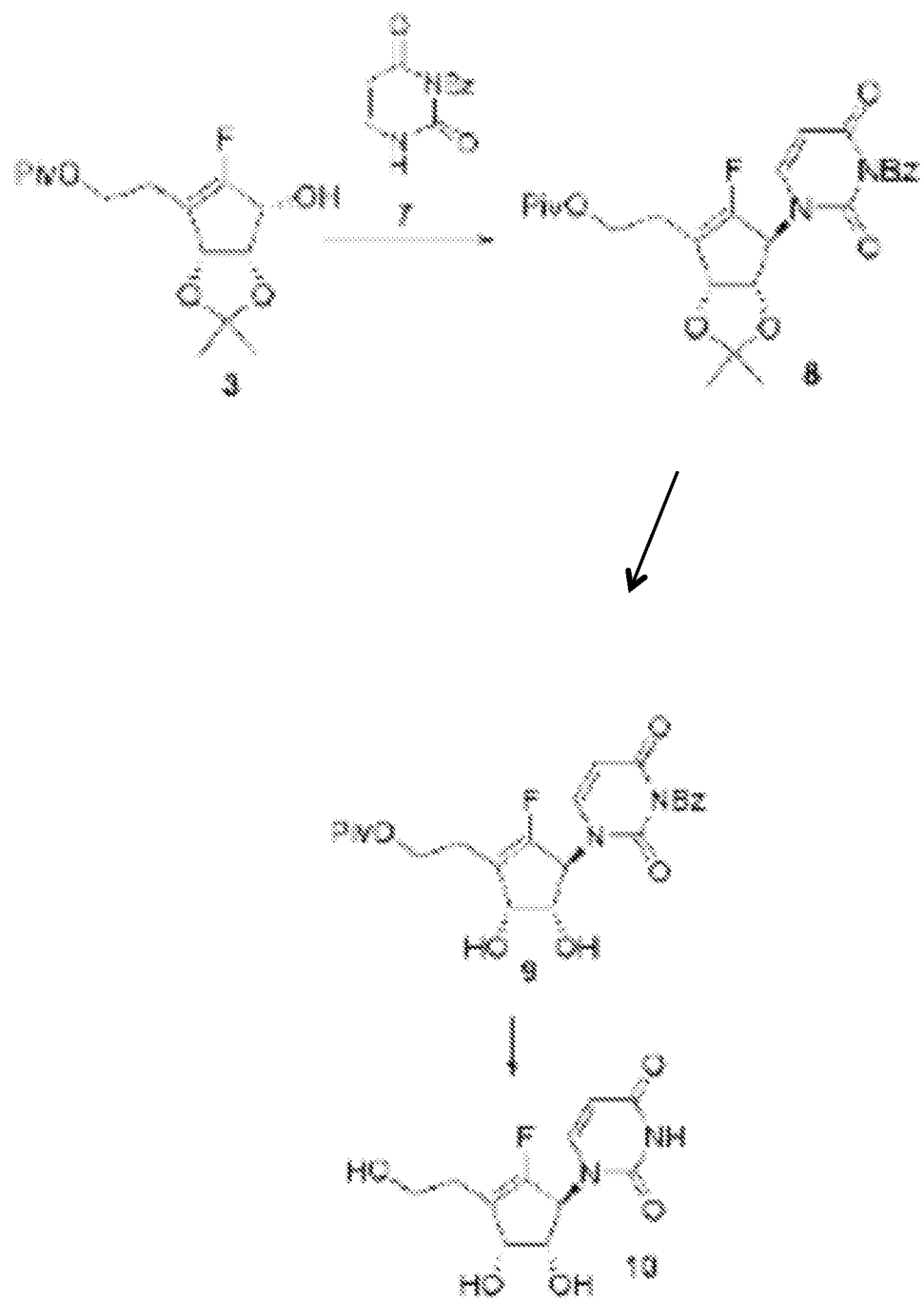
FIG. 4 is chemical scheme IV for the synthesis of (1S,2R,5S)-4-Fluoro-3-hydroxyethyl-5-(uracil-1-yl)-cyclopent-3(4)-en-1,2-diol (Compound 10).
Figure 5:
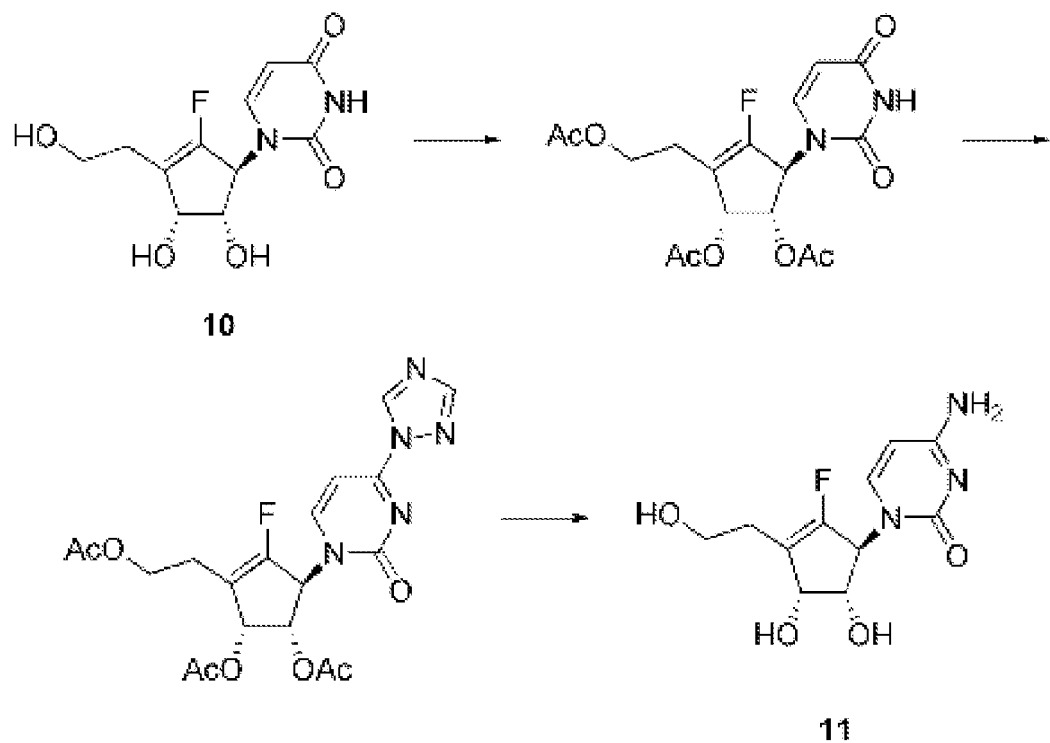
FIG. 5 is chemical scheme V for the synthesis of (1S,2R,5S)-5-(Cytosine-1-yl)-4-fluoro-3-hydroxyethyl-cyclopent-3(4)-en-1,2-diol (Compound 11)
Figure 6A:
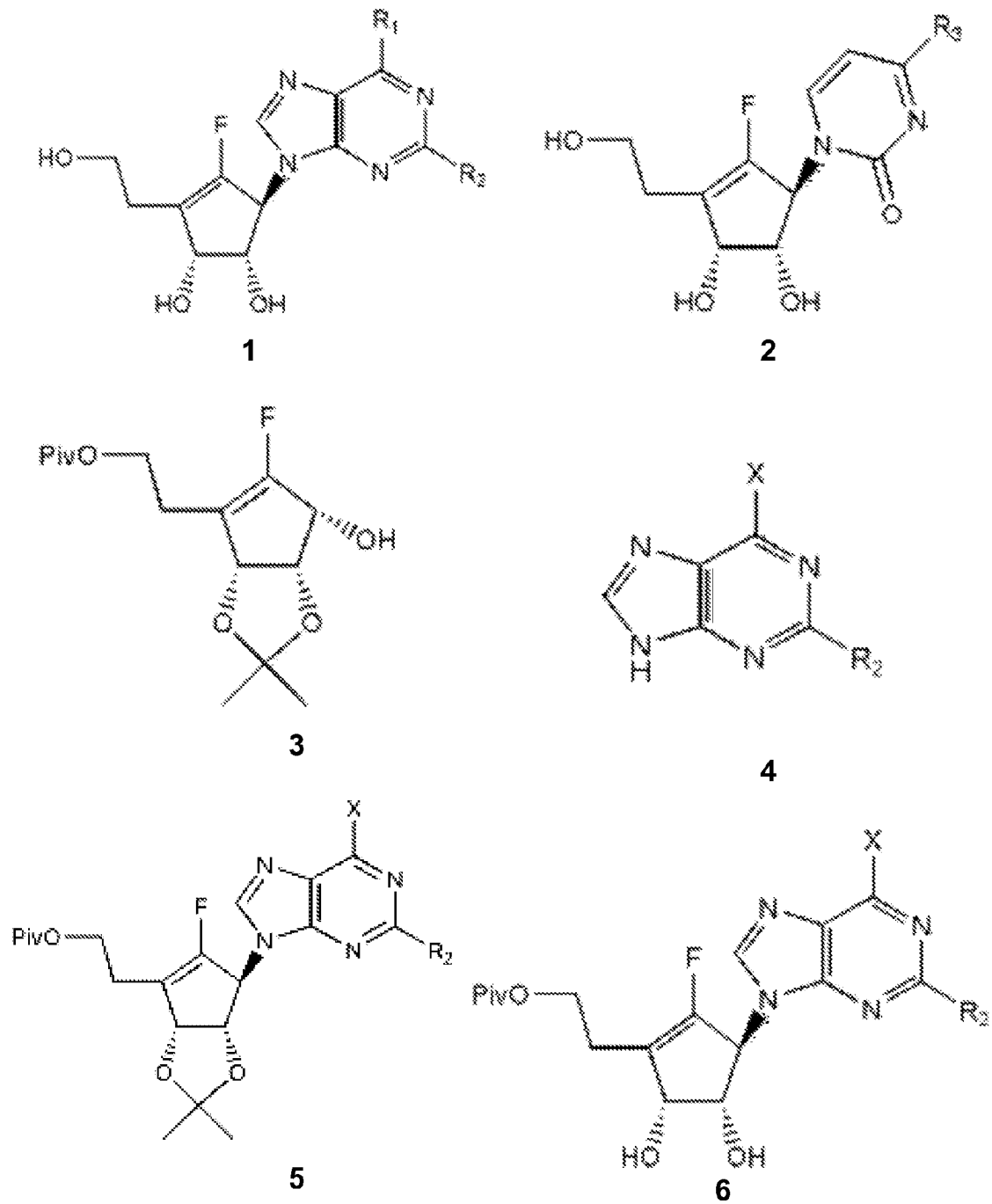
Figure 6B:
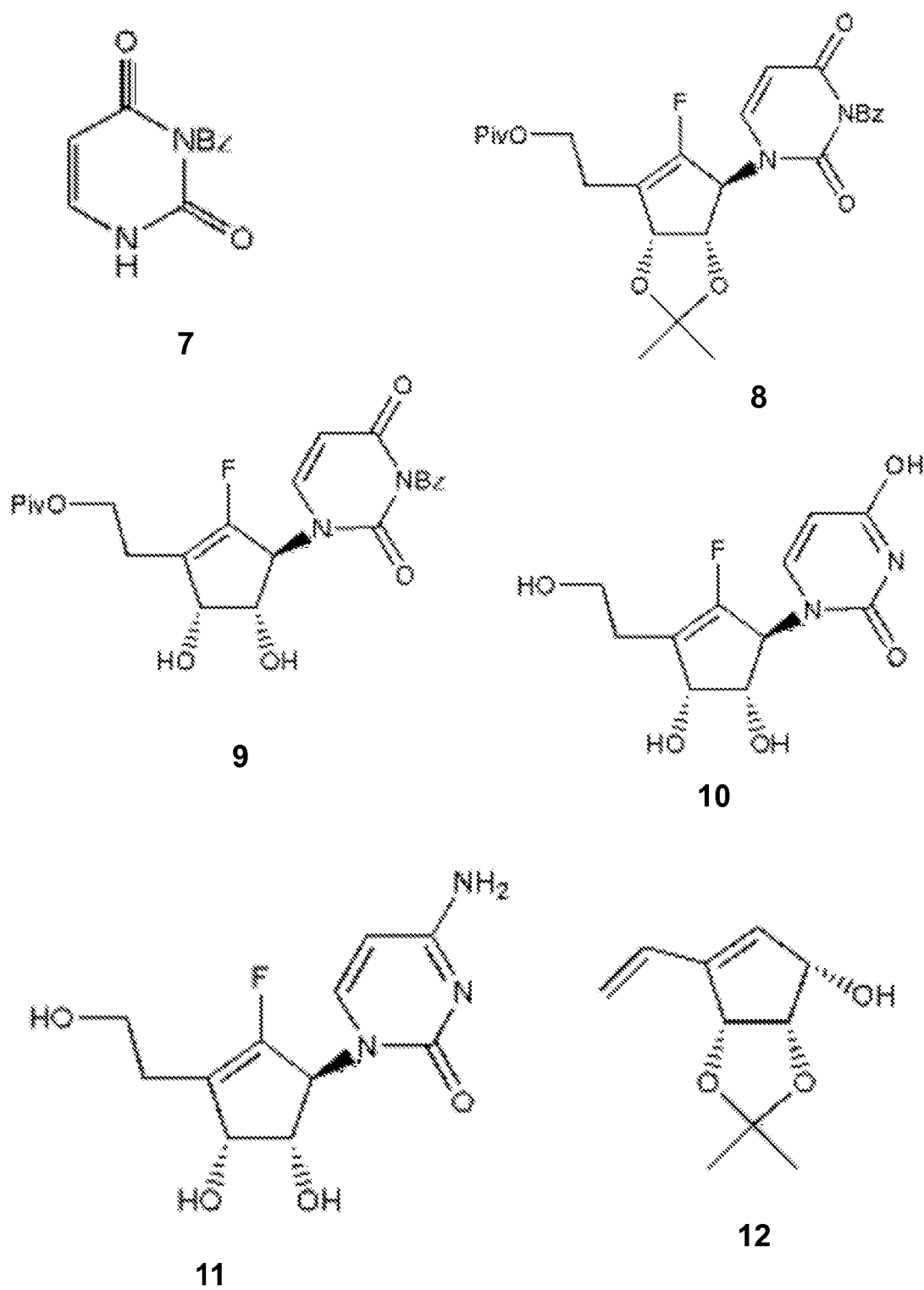

In addition, the present invention provides the method for preparing (1S,2R,5S)-4-Fluoro-3-hydroxyethyl-5-(uracil-1-yl)-cyclopent-3(4)-en-1,2-diol (Compound 10). The method steps comprise preparing the intermediate compound (Compound 8) by reacting 2,2-Dimethyl-propionic acid 2-[(3S,4R, 5S)-2-fluoro-4,5-(O-isopropylidenedioxy)-3-oxocyclopent-1(2)-en]-ethyl ester (Compound 3) with 3-N-benzoyluracil (Compound 7); preparing 2,2-Dimethyl-propionic acid 2-[(2R,3S,4S)-4-(3-benzoyl-uracil-1-yl)-5-fluoro-2,3-dihydroxy cyclopent-1(5)-en]-ethyl ester (Compound 9) by reacting the intermediate compound (Compound 8) with an acid; and preparing (1S,2R,5S)-4-Fluoro-3-hydroxyethyl-5-(uracil-1-yl)-cyclopent-3(4)-en-1,2-diol (Compound 10) by removing the protecting group from 2,2-Dimethyl-propionic acid 2-[(2R,3S,4S)-4-(3-benzoyl-uracil-1-yl)-5-fluoro-2,3-dihydroxy cyclopent-1(5)-en]-ethyl ester (Compound 9). To synthesize pyrimidine nucleoside, the intermediate compound 2-[(3S,4R,5S)-2-fluoro-4,5-(O-isopropylidenedioxy)-3-oxocyclopent-1(2)-en]-ethyl ester (Compound 3) is condensed with n-benzoyl uracil then processed with an acid, yielding 2,2-Dimethyl-propionic acid 2-[(2R,3S,4S)-4-(3-benzoyl-uracil-1-yl)-5-fluoro-2,3-dihydroxycyclopent-1(5)-en]-ethyl ester (Compound 9). The resultant 2,2-Dimethyl-propionic acid 2-[(2R, 3S,4S)-4-(3-benzoyl-uracil-1-yl)-5-fluoro-2,3-dihydroxycyclopent-1(5)-en]-ethyl ester (Compound 9) is processed with NaOMe and the protecting group is removed to prepare the final compound (1S,2R,5S)-4-Fluoro-3-hydroxyethyl-5-(uracil-1-yl)-cyclopent-3(4)-en-1,2-diol (Compound 10). Also, the present invention enables the preparation of cytosine compound (1S,2R,5S)-5-(Cytosine-1-yl)-4-fluoro-3-hydroxyethyl-cyclopent-3(4)-en-1, 2-diol (Compound 11) by reacting (1S,2R,5S)-4-Fluoro-3-hydroxyethyl-5-(uracil-1-yl)cyclopent-3(4)-en-1,2-diol (Compound 10) with 1) $POCl_3$, $NEt_3$, 1,2,4-triazole, 2) $NH_4OH$, 1,4-dioxane, and 3) $NH_3$, MeOH. These preparation methods according to the present invention are schematically shown in FIGS. 4-5.

Figure 2:
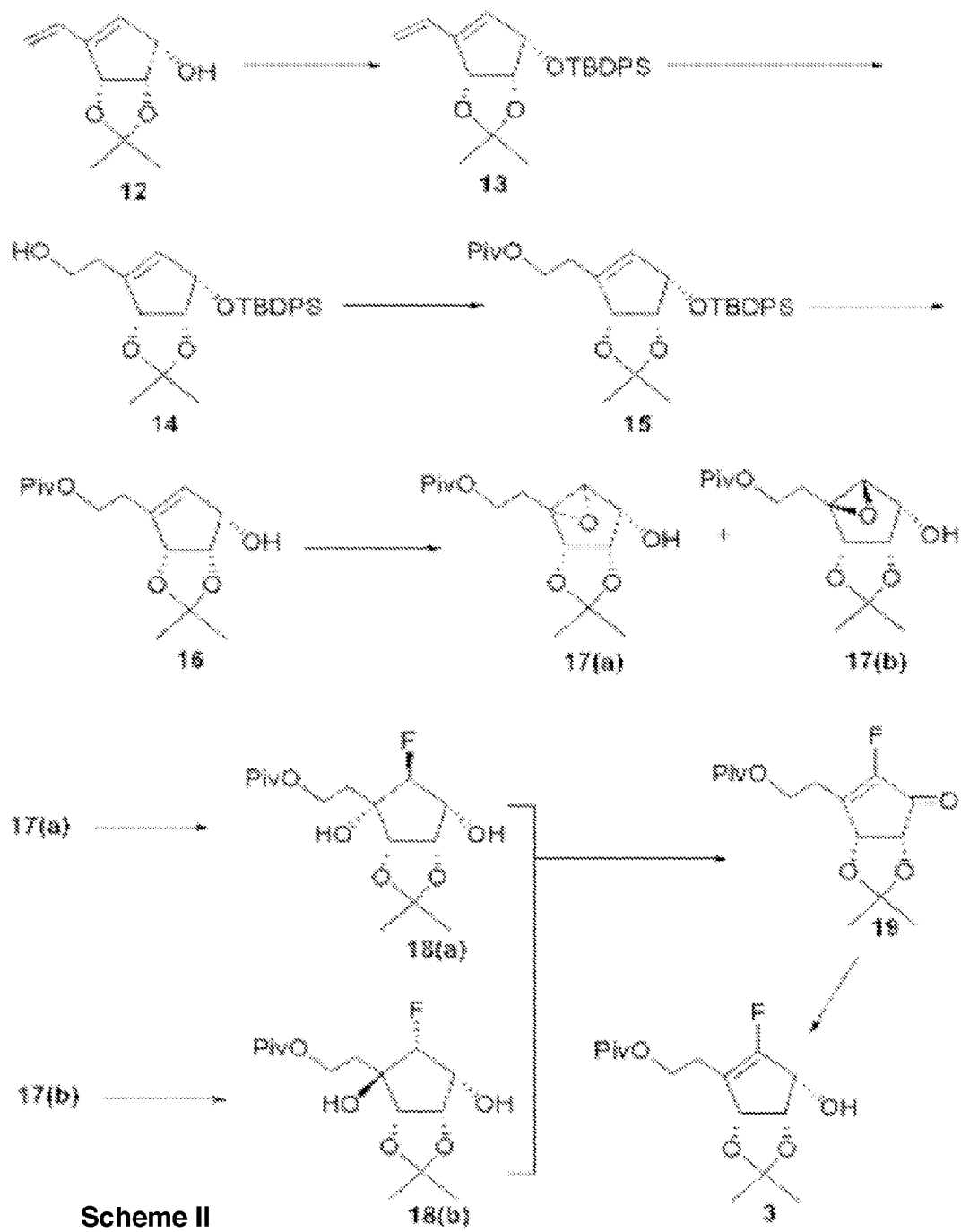
FIG. 2 is chemical scheme II for the synthesis of 2,2-Dimethyl-propionic acid 2-[(3S,4R,5S)-2-fluoro-4,5-(O-isopropylidenedioxy)-3-ol cyclopent-1(2)-en]ethyl ester (Compound 3).

The present invention also provides the method for synthesizing or preparing 2,2-Dimethyl-propionic acid 2-[(3S,4R, 5S)-2-fluoro-4,5-(O-isopropylidenedioxy)-3-oxocyclopent-1(2)-en]-ethyl ester (Compound 3), comprising the step of preparing (2R,3S,4S)-4-(tert-Butyldiphenylsilyloxy)-1-ethenyl-2,3-(O-isopropylidenedioxy)-1-cyclopentene (Compound 13) by reacting (1S,4R,5S)-3-Ethenyl-4,5-(O-isopropylidenedioxy)-4-cyclopent-2(3)-en-1-ol (Compound 12) with TBDPSCl; preparing [(2R,3S,4S)-4-(tert-Butyldiphenylsilyloxy)-2,3-(O-isopropylidenedioxy)-1-cyclopentene]ethanol (Compound 14) by reacting (2R,3S,4S)-4-(tert-Butyldiphenylsilyloxy)-1-ethenyl-2,3-(O-isopropylidenedioxy)-1-cyclopentene (Compound 13) with 9-BBN and sodium perborate; preparing 2-[(2R,3S,4S)-4-(tert-butyldiphenylsilanyloxy)-2,3-(O-isopropylidenedioxy)-cyclopent-1(5)-enyl]-ethyl ester (Compound 15) by reacting [(2R,3S,4S)-4-(tert-Butyldiphenylsilyloxy)-2,3-(O-isopropylidene dioxy)-1-cyclopentene]ethanol (Compound 14) with pivalonyl chloride; preparing 2,2-Dimethyl-propionic acid 2-[(3S,4S,5R)-4,5-(O-isopropylidenedioxy)-cyclopent-3-ol]-ethyl ester (Compound 16) by reacting 2-[(2R,3S,4S)-4-(tert-butyldiphenylsilanyloxy)-2,3-(O-isopropylidenedioxy)-cyclopent-1(5)-enyl]-ethyl ester (Compound 15) with n-Bu$_4$NF and eliminating traces of TBDPS; preparing 2,2-Dimethyl-propionic acid 2-[(1R,2R,3R,4R,5S)-4,5-(O-isopropylidenedioxy)-1(2)oxirane-cyclopent-3-ol]-ethyl ester (Compound 17a) and 2,2-Dimethyl-propionic acid 2-[(1S,2S,3R,4R,5S)-4,5-(O-isopropylidenedioxy)-1(2)oxirane-cyclopent-3-ol]-ethyl ester (Compound 17b) by reacting 2,2-Dimethyl-propionic acid 2-[(3S,4S,5R)-4,5-(O-isopropylidenedioxy)-cyclopent-3-ol]-ethyl ester with m-CPBA; preparing 2,2-Dimethyl-propionic acid 2-[(1R,2S,3R,4R,5S)-2-fluoro-4,5-(O-isopropylidenedioxy)-cyclopent-1,3-diol]-ethyl ester and 2-[(1S,2R,3R,4R,5S)-2-fluoro-4,5-(O-isopropylidenedioxy)-cyclopent-1,3-diol]ethyl ester (Compound 18b) by reacting 2,2-Dimethyl-propionic acid 2-[(1R,2R,3R,4R,5S)-4,5-(O-isopropylidenedioxy)-1(2)oxirane-cyclopent-3-ol]-ethyl ester (Compound 17a) or 2,2-Dimethyl-propionic acid 2-[(1S,2S,3R,4R,5S)-4,5-(O-isopropylidenedioxy)-1(2)oxirane-cyclopent-3-ol]-ethyl ester (Compound 17b) with tetra-n-butylammonium hydrogen fluoride (n-Bu$_4$NH$_2$F$_3$) and KHF$_2$; preparing 2,2-Dimethyl-propionic acid 2-[(4R,5S)-2-fluoro-4,5-(O-isopropylidenedioxy)-3-oxocyclopent-1(2)-en]-ethyl ester (Compound 19) by oxidizing 2,2-Dimethyl-propionic acid 2-[(1R,2S,3R,4R,5S)-2-fluoro-4,5-(O-isopropylidenedioxy)-cyclopent-1,3-diol]-ethyl ester or 2-[(1S,2R,3R,4R,5S)-2-fluoro-4,5-(O-isopropylidenedioxy)-cyclopent-1,3-diol]-ethyl ester (Compound 18b); and preparing 2-[(3S,4R,5S)-2-fluoro-4,5-(O-isopropylidene dioxy)-3-oxocyclopent-1(2)-en]-ethyl ester (Compound 3) by reacting 2,2-Dimethyl-propionic acid 2-[(4R,5S)-2-fluoro-4,5-(O-isopropylidenedioxy)-3-oxocyclopent-1(2)-en]-ethyl ester (Compound 19) with NaBH$_4$. The preparation method according to the present invention is schematically shown in FIG. 2. Also, the present invention provides the intermediate compound 2-[(3S,4R,5S)-2-fluoro-4,5-(O-isopropylidenedioxy)-3-oxocyclopent-1(2)-en]ethyl ester (Compound 3) to prepare the fluoro-homoneplanocin A and its nucleoside derivatives, as described herein.

The (1S,4R,5S)-3-Ethenyl-4,5-(O-isopropylidenedioxy)-4-cyclopent-2(3)-en-1-ol (Compound 12) is processed with TBDPSCl to prepare (2R,3S,4S)-4-(tert-Butyldiphenylsilyloxy)-1-ethenyl-2,3-(O-isopropylidenedioxy)-1-cyclopentene (Compound 13), which is then processed with 9-BBN and sodium perborate to synthesize the reduced (78%) [(2R,3S,4S)-4-(tert-Butyldiphenylsilyloxy)-2,3-(O-isopropylidenedioxy)-1-cyclopentene]ethanol (Compound 14). The [(2R,3S,4S)-4-(tert-Butyldiphenylsilyloxy)-2,3-(O-isopropylidenedioxy)-1-cyclopentene]ethanol (Compound 14) is processed with pivalonyl chloride and traces of TBDPS are eliminated to synthesize 2,2-Dimethyl-propionic acid 2-[(3S,4S,5R)-4,5-(O-isopropylidenedioxy)-cyclopent-3-ol]-ethyl ester (Compound 16). The 2,2-Dimethyl-propionic acid 2-[(3S,4S,5R)-4,5-(O-isopropylidenedioxy)-cyclopent-3-ol]-ethyl ester (Compound 16) is processed with mCPBA to prepare 2,2-Dimethyl-propionic acid 2-[(1R,2R,3R,4R,5S)-4,5-(O-isopropylidenedioxy)-1(2)oxirane-cyclopent-3-ol]-ethyl ester (Compound 17a) in a-epoxide form (71%) and 2,2-Dimethyl-propionic acid 2-[(1S,2S,3R,4R,5S)-4,5-(O-isopropylidenedioxy)-1(2)oxirane-cyclopent-3-ol]-ethyl ester (Compound 17b) in β-epoxide form (8.6%). The 2,2-Dimethyl-propionic acid 2-[(1R,2R,3R,4R,5S)-4,5-(O-isopropylidenedioxy)-1(2)oxirane-cyclopent-3-ol]-ethyl ester (Compound 17a) or 2,2-Dimethyl-propionic acid 2-[(1S,2S,3R,4R,5S)-4,5-(O-isopropylidenedioxy)-1(2)oxirane-cyclopent-3-ol]-ethyl ester (Compound 17b) is processed with tetra-n-butylammonium hydrogen fluoride (n-Bu$_4$NH$_2$F$_3$) and KHF$_2$ to prepare 2,2-Dimethyl-propionic acid 2-[(1R,2S,3R,4R,5S)-2-fluoro-4,5-(O-isopropylidenedioxy)-cyclopent-1,3-diol]-ethyl ester (Compound 18a) and 2,2-Dimethyl-propionic acid 2-[(1S,2R,3R,4R,5S)-2-fluoro-4,5-(O-isopropylidenedioxy)-cyclopent-1,3-diol]-ethyl ester, which are oxidized to prepare 2,2-Dimethyl-propionic acid 2-[(4R,5S)-2-fluoro-4,5-(O-isopropylidenedioxy)-3-oxocyclopent-1(2)-en]-ethyl ester (Compound 19). The 2,2-Dimethyl-propionic acid 2-[(4R,5S)-2-fluoro-4,5-(O-isopropylidenedioxy)-3-oxocyclopent-1(2)-en]-ethyl ester (Compound 19) is processed with NaBH$_4$ to synthesize 2,2-Dimethyl-propionic acid 2-[(3S,4R,5S)-2-fluoro-4,5-(O-isopropylidenedioxy)-3-oxocyclopent-1(2)-en]-ethyl ester (Compound 3), the glycosyl provider.

Figure 1:
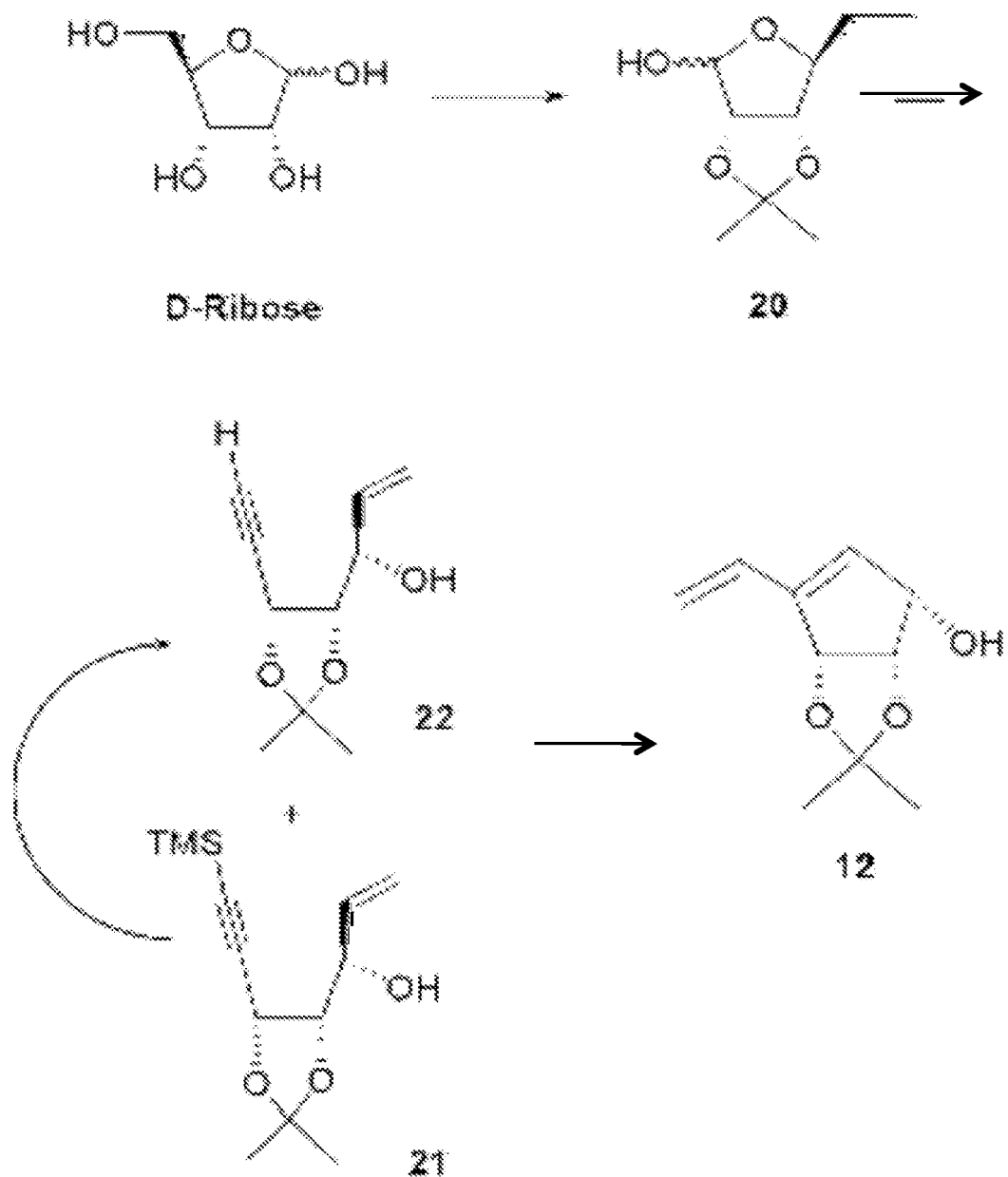
FIG. 1 is chemical scheme I for the synthesis of (1S,4R,5S)-3-Ethenyl-4,5-(O-isopropylidenedioxy)-4-cyclopent-2(3)-en-1-ol (Compound 12).

In addition, the invention provides the method for synthesizing or preparing (1S,4R,5S)-3-Ethenyl-4,5-(O-isopropylidenedioxy)-4-cyclopent-2(3)-en-1-ol (Compound 12). The method steps comprise using condensation reaction on a D-ribose product (Compound 20) with trimethylsilyldiazomethane, under the condition that n-BuLi and N,N-diisopropylamine (DIPA) exists, to prepare (3S,4S,5R)-4,5-(O-Isopropylidenedioxy)-hept-1-en-6-(2-trimethylsilanylethynyl)-3-ol (Compound 21) and (3S,4S,5R)-4,5-(O-Isopropylidene dioxy)-hept-1-en-6-yn-3-ol) (Compound 22); reacting (3S,4S,5R)-4,5-(O-Isopropylidenedioxy)-hept-1-en-6-(2-trimethylsilanylethynyl)-3-ol (Compound 21) with tetra-n-butylammonium fluoride to convert into (3S,4S,5R)-4,5-(O-Isopropylidenedioxy)-hept-1-en-6-yn-3-ol) (Compound 22); using Grubbs' catalyst on (3S,4S,5R)-4,5-(O-Isopropylidenedioxy)-hept-1-en-6-yn-3-ol) (Compound 22) to prepare Compound 12 using ring-closing reaction. The preparation method according to the present invention is schematically shown in FIG. 1. Also, the present invention also provides the intermediate compound of (1S,4R,5S)-3-Ethenyl-4,5-(O-isopropylidenedioxy)-4-cyclopent-2(3)-en-1-ol (Compound 12) to prepare the fluoro-homoneplanocin A and its nucleoside derivative, as described herein.

The D-ribose product (Compound 20) is synthesized from D-Ribose, using a well-known method in the art. Condensing D-ribose product (Compound 20) with trimethylsilyldiazomethane in the presence of n-BuLi and N,N-diisopropylamine (DIPA), the compound of (3S,4S,5R)-4,5-(O-Isopropylidenedioxy)-hept-1-en-6-yn-3-ol) (Compound 22) (65%) and (3S,4S,5R)-4,5-(O-Isopropylidenedioxy)-hept-1-en-6-(2-trimethylsilanylethynyl)-3-ol (Compound 21), TMS derivatives (16%) are synthesized. The (3S,4S,5R)-4,5-(O-Isopropylidenedioxy)-hept-1-en-6-(2-trimethylsilanylethynyl)-3-ol (Compound 21) changes into the identical substance, (3S,4S,5R)-4,5-(O-Isopropylidenedioxy)-hept-1-en-6-yn-3-ol) (Compound 22), by processing with tetra-n-butylammonium fluoride (TBAF). The (3S,4S,5R)-4,5-(O-Isopropylidenedioxy)-hept-1-en-6-yn-3-ol) (Compound 22)

is processed with Grubbs' catalyst to synthesize the compound of Compound 12 (60%) through ring-closing metathesis.

In addition, the present invention provides the compound of Formula 1, or a pharmacological or pharmaceutical composition thereof or the pharmacologically acceptable salts thereof for prevention or treatment of cancer. The pharmacological or pharmaceutical composition may further comprise a pharmacologically or pharmaceutically acceptable carrier.

As used herein, the term "subject" refers to any recipient of the compounds of Formula 1 or Formula 2 or the pharmacologically acceptable salts or pharmaceutical compositions thereof. Also, in the present invention, cancer maybe colorectal cancer, prostate cancer, breast cancer, gastric cancer, lung cancer, or blood cancer.

As used herein, the term "pharmacologically acceptable salts" refers to the salts prepared by using standard procedures in the art, where such preparation methods are known to persons skilled in the art. Specifically, pharmacologically acceptable salts include, but are not limited to, the salts derived from pharmacologically and/or physiologically acceptable organic and inorganic acids, and bases. Suitable acids include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulphonic acid, tartaric acid, acetic acid, citric acid, methanesulfonic acid, formic acid, benzoic acid, malonic acid, naphthalene-2-sulfonic acid, and benzenesulfonic acid, etc. The salts derived from suitable bases include alkali metals, such as sodium or potassium, and alkali earth metals such as magnesium.

In the preparation of dosage form of compound for treatment or prevention of cancer in the present invention, it is preferable to mix or dilute the active component with carrier, or seal it in carrier of a container form. Also, it is possible to use the composition for drug addiction treatment in the present invention by Formulating for oral administration in the form of as powder, granule, tablet, capsule, suspension, emulsion, syrup or aerosol, external application, suppository, or sterile injection according to the conventional methods, respectively. Specifically, in the case of Formulation, it is possible to prepare the compound using a conventionally used diluent or diluting agent, such as inert filler, weighting agent, bonding agent, wetting agent, disintegrating agent, or surfactant agent. The solid Formulation agent for oral administration includes, but is not limited to, tablet, pill, powder, granule, and capsule. Such a solid Formulation agent can also be prepared in conjunction with one or more diluting agents, such as starch, calcium carbonate, sucrose, lactose, or gelatin. It is also possible to use a lubricant, such as magnesium stearate or talc, besides a simple diluting agent. In addition, it is possible to prepare by adding various diluting agents, such as a wetting agent, a sweetening agent, a flavoring agent, or a preserving agent, in addition to dietetic water or liquid paraffin, for oral administration. The Formulation agent for non-oral administration includes sterile aqueous solution, non-aqueous solvent, suspending agent, emulsion, lyophilization agent and suppository agent. Vegetable oils such as propylene glycol, polyethylene glycol, or olive oil, or an ester such as ethyl oleate, can be used as a non-aqueous solvent. Witepsol, macrogol, Twin 61, cacao butter, laurinum, or glycerogelatin can be used as a suppository base.

In the present invention, "prevention" refers to any action that can suppress the occurrence of cancer by administration of the compound, while "treatment" refers to any action that can improve or change the symptoms of the cancer for the better.

The compound for treatment and/or prevention of cancer in the present invention can be administered both orally and aborally (for example, intravenously, subcutaneously, within the peritoneal cavity or locally); dosage, which depends on the condition of the patient, as well as the patient's weight, progression of the disease, medicinal type, and administration type, can be determined properly by the physician.

The compound for treatment and/or prevention of cancer in the present invention can be formulated for oral administration in the form of powder, granule, tablet, capsule, suspension, emulsion, syrup or aerosol, external application, suppository, or sterile injection. Specifically, in the case of Formulation, it is possible to prepare the compound using a conventionally used diluent or diluting agent, such as inert filler, weighting agent, bonding agent, wetting agent, disintegrating agent, or surfactant agent. The solid Formulation agent for oral administration includes, but is not limited to, tablet, pill, powder, granule and capsule. Such a solid Formulation agent can be prepared in conjunction with one or more diluting agents, such as starch, calcium carbonate, sucrose, lactose, or gelatin. It is also possible to use a lubricant, such as magnesium stearate or talc, instead of a simple diluting agent. In addition, it is possible to prepare by adding various diluting agents, such as wetting agent, sweetening agent, flavoring agent, or preserving agent, in addition to dietetic water or liquid paraffin, for oral administration. The Formulation agent for non-oral administration includes sterile aqueous solution, non-aqueous solvent, suspending agent, emulsion, lyophilization agent or suppository agent. Vegetable oils such as propylene glycol, polyethylene glycol, or olive oil, or an ester such as ethyl oleate, can be used as a non-aqueous solvent. Witepsol, macrogol, twin6l, cacao butter, laurinum, or glycerogelatin can be used as suppository agent.

The compound for treatment and/or prevention of cancer in the present invention can be administered both orally and aborally (for example, intravenously, subcutaneously, within the peritoneal cavity or locally); dosage, which depends on the condition of the patient, as well as the patient's weight, progression of the disease, medicinal type, and administration type, can be determined properly by the physician.

Also, desirably, the compound in the present invention can be formulated using well-known methods to provide rapid, continued, or delayed release of the active component after administered to mammals. The dosage of the active component such as the compound represented by Formula 1 in the present invention or its pharmacologically accepted salts is determined by the physician in accord with the subject, the seriousness of the disease or condition, and administration speed. As active component, the compound represented by Formula 1 can be administered orally or aborally to mammals including humans at a daily dosage (or divided doses) from 1 mg/kg to 100 mg/kg animal body weight, while 5 mg/kg to 50 mg/kg animal body weight is desirable. In certain cases, less than the above-mentioned dosage may be appropriate, while larger doses may be used with no side effects; for larger doses, it would be administered in divided doses throughout the day.

The compounds of Formula 1 in the present invention can be the pharmacologically acceptable salts thereof, and also all of the solvents and hydrates that can be prepared from the same. These solvents and hydrates of the compound of Compound 1 can be prepared from the compound of Formula 1 using conventional procedures.

The compounds of Formula 1 according to the present invention can also be prepared as crystalline or amorphous form; when the compounds of Formula 1 is prepared as crystalline form, it can be randomly hydrated or solvated. The compound of the present invention may refer to the compound comprising not only stoichiometric amount of hydrates of the compounds of Formula 1 but also various amounts of water. The solvent for the compounds of Formula 1 according to the present invention includes both stoichiometric amounts and non-stoichiometric amounts of solvents.

According to trial implementation of the present invention, the administration of fluoro-homoneplanocin A to the cancer cells was shown to impede the growth of cells in the colorectal cancer, prostate cancer, breast cancer, gastric cancer, lung cancer and blood cancer; its anticarcinogenic effect was found to be similar to Gemcitabine, the widely-used anticancer medicine.

According to the preparation methods of the present invention, it was achieved to synthesize fluoro-homoneplanocin A by combining fluoro-neplanocin A with homoneplanocin A, which was difficult to synthesize using the conventional methods, and to synthesize the uracil or cytosine-substituted nucleoside derivative using them. In addition, the treatment of the cancer cells with fluoro-homoneplanocin A showed its effect to inhibit the growth of cancer cells and, particularly, comparison of its efficacy with that of Gemcitabine, the widely-used anticancer drug, showed the similar level of its anticancer activity as that of Gemcitabine.

The present invention is described in more details through providing Examples as below. However these Examples are merely meant to illustrate, but in no way to limit, the claimed invention.

EXAMPLE 1

Preparation of (3S,4S,5R)-4,5-(O-Isopropylidenedioxy)-hept-1-en-6-(2-trimethylsilanylethynyl)-3-ol (Compound 21) and ((3S,4S,5R)-4,5-(O-Isopropylidenedioxy)-hept-1-en-6-yn-3-ol) (Compound 22)

As per chemical scheme I (FIG. 1), after dissolving diisopropylamine (26.4 mL, 361.35 mmol) in anhydrous THF (300 mL), n-BuLi (70 mL, 2.5 M, 757.25 mmol in toluene) was added at $-78°$ C. and then stirred for 30 minutes. TMSCHN$_2$ (53.2 mL, 2 M, 106.33 mmol in hexane) was added to the LDA solution prepared in this way at $-78°$ C., and then stirred for 1 hour. The solution resulted from dissolving Compound 20 (13.2 g, 70.88 mmol) in anhydrous THF (55 mL) was added to the resultant solution at $-78°$ C., stirred for 30 minutes and then stirred further for 12 hours at room temperature. After completion of the reaction, NH$_4$Cl solution was added to the reaction mixture, which was then extracted with ethyl acetate. The organic layer was dehydrated by adding anhydrous MgSO$_4$ after washing with brine. Compound 21 (2.88 g, 16%) and Compound 22 (8.40 g, 65%) were obtained in the form of oil by separating the residue, obtained through the distillation of the filtered solution under reduced pressure, with silica gel column (EtOAc:hexane=3:1).

Compound 21: $[\alpha]^{24.4}{}_D$ $-3.81°$ (c 28.8, CH$_2$Cl$_2$); $^1$H NMR (400 MHz, CDCl$_3$)d 0.00 (s, 9H), 1.32 (s, 3H), 1.54 (s, 3H), 2.30 (d, J=4.8, 1H), 3.75 (dd, J$_1$=8.4, J$_2$=6.0, 1H), 4.18-4.23 (m, 1H), 4.68 (d, J=6.0 Hz, 1H), 5.09 (dt, J$_1$=10.8, J$_2$=1.6 Hz, 1H), 5.23 (dt, J$_1$=17.2, J$_2$=1.6 Hz, 1H), 5.86 (ddd, J$_1$=17.2, J$_2$=10.8, J$_3$=5.2 Hz, 1H); C (100 MHz, CDCl$_3$) d-0.15, 25.92, 27.67, 68.23, 72.07, 80.64, 94.67, 101.08, 110.90, 116.67, 137.08; HRMS (ESI) C$_{13}$H$_{23}$O$_3$Si: 255.1332, (M+H)$^+$: 255.1405.

Compound 22: $[\alpha]24.2_D$ $-0.45°$ (c 2.2, CH$_2$Cl$_2$); $^1$H NMR (400 MHz, CDCl$_3$) d 1.35 (s, 3H), 1.54 (s, 3H), 2.14 (d, J=4.8 Hz, 1H), 2.65 (d, J=2.4 Hz, 1H), 3.98 (dd, J$_1$=5.6, J$_2$=8.4 Hz, 1H), 4.42-4.45 (m, 1H), 4.91 (dd, J$_1$=6.0, J$_2$=2.4 Hz, 1H), 5.30 (dt, J$_1$=10.8, J$_2$=1.2 Hz, 1H), 5.44 (dt, J$_1$=17.6, J$_2$=1.2 Hz, 1H), 6.08 (ddd, J$_1$=17.2, J$_2$=10.4, J$_3$=5.2 Hz, 1H); $^{13}$C (100 MHz, CDCl$_3$) d 26.10, 27.67, 68.23, 72.12, 76.62, 80.19, 80.42, 111.21, 116.82, 137.43; HRMS (ESI) C$_{10}$H$_{14}$O$_3$Na: 205.0945, (M+Na)$^+$: 205.0826.

Conversion of (3S,4S,5R)-4,5-(O-Isopropylidenedioxy)-hept-1-en-6-(2-trimethylsilanylethynyl)-3-ol (Compound 21) to (3S,4S,5R)-4,5-(O-Isopropylidenedioxy)-hept-1-en-6-yn-3-ol (Compound 22)

As per chemical scheme I (FIG. 1), after dissolving (3S,4S,5R)-4,5-(O-Isopropylidenedioxy)-hept-1-en-6-(2-trimethylsilanylethynyl)-3-ol (Compound 21) in THF (70 mL), tetrabutyl-n-ammonium fluoride (solution of 1M in THF, 4 mL, 15.56 mmol) was added at 0° C., and then was stirred for 2 hours at room temperature. (3S,4S,5R)-4,5-(O-Isopropylidenedioxy)-hept-1-en-6-yn-3-ol (Compound 22) (0.94 g, 71%) was obtained in the form of colorless liquid by separating the residue, obtained through distillation of the reaction mixture under reduced pressure, with silica gel column (EtOAc:hexane=2:1).

Preparation of (1S,4R,5S)-3-Ethenyl-4,5-(O-isopropylidenedioxy)-4-cyclopent-2(3)-en-1-ol (Compound 12)

As per chemical scheme I (FIG. 1), after dissolving (3S,4S,5R)-4,5-(O-Isopropylidenedioxy)-hept-1-en-6-yn-3-ol (Compound 22) (3 g, 16.46 mmol) in anhydrous CH$_2$Cl$_2$ (400 mL), Grubbs' catalyst (813 mg, 0.937 mmol) was applied. The above solution was stirred for 24 hours at room temperature in the presence of ethylene gas. (1S,4R,5S)-3-Ethenyl-4,5-(O-isopropylidenedioxy)-4-cyclopent-2(3)-en-1-ol (Compound 12) (1.8 g, 60%) was obtained in the form of solid by separating the residue obtained through enrichment of the filtrate under reduced pressure after filtering the above reaction mixture on a celite with silica gel column (EtOAc:hexane=2:1).

$[\alpha]^{24.5}{}_D$ 22.0° (c 1.8, CH$_2$Cl$_2$): $^1$H NMR (400 MHz, CDCl$_3$) d 1.40 (s, 3H), 1.41 (s, 3H), 2.73 (d, J=9.6 Hz, 1H), 4.54-4.61 (m, 1H), 4.75 (pseudo t, J=5.6 Hz, 1H), 5.14 (d, J=5.6 Hz, 1H), 5.29 (d, J=10.8 Hz, 1H), 5.56-5.61 (m, 1H), 5.72-5.76 (m, 1H), 6.41 (dd, J$_1$=17.6, J$_2$=10.8 Hz, 1H): $^{13}$C (100 MHz, CDCl$_3$) d 26.77, 27.67, 73.37, 77.66, 82.80, 112.77, 119.17, 130.77, 133.52, 142.89; HRMS (ESI) C$_{10}$H$_{14}$O$_3$Na: 205.0945, (M+Na)$^+$: 205.0826.

EXAMPLE 2

Preparation of (2R,3S,4S)-4-(tert-Butyldiphenylsilyloxy)-1-ethenyl-2,3-(O-isopropylidenedioxy)-1-cyclopentene (Compound 13)

As per chemical scheme II (FIG. 2), after dissolving (1S,4R,5S)-3-Ethenyl-4,5-(O-isopropylidenedioxy)-4-cyclopent-2(3)-en-1-ol (Compound 12) (1.0 g, 5 mmol) in anhydrous DMF (15 mL), imidazole (0.746 g, 10.98 mmol) and t-Butyldiphenylsilyl chloride (1.40 mL, 6.03 mmol) were added at −10° C., stirred for 10 minutes, and then stirred further for 10 hours at room temperature. After diluting with water, the reaction mixture was extracted with ether. The organic layer was dehydrated by adding anhydrous MgSO$_4$ after washing with brine. (2R,3S,4S)-4-(tert-Butyldiphenylsilyloxy)-1-ethenyl-2,3-(O-isopropylidenedioxy)-1-cyclopentene (Compound 13) (2.0 g, 90%) was obtained in the form of colorless oil by separating the residue, obtained through distillation of the resultant under reduced pressure after filtering the above solution, with silica gel column (EtOAc:hexane=9:1).

$[\alpha]^{19.0}{}_D$ +54° (c 2.0, CH$_2$Cl$_2$); $^1$H NMR (400 MHz, CDCl$_3$) d 1.09 (s, 9H), 1.40 (s, 3H), 1.47 (s, 3H), 4.42 (pseudo t, J=5.6 Hz, 1H), 4.57-4.59 (m, 1H), 4.96 (d, J=6.0 Hz, 1H), 5.23-5.26 (m, 1H), 5.54-5.55 (m, 1H), 5.58-5.60 (m, 1H), 6.38 (dd, $J_1$=17.6, $J_2$=11.8 Hz, 1H), 7.36-7.46 (m, 6H), 7.73-7.75 (m, 2H), 7.79-7.81 (m, 2H); $^{13}$C NMR (100 MHz, CDCl$_3$) d 19.55, 27.05, 27.22, 75.17, 78.64, 82.54, 112.38, 118.55, 127.81, 127.72, 129.84, 129.88, 131.09, 133.55, 134.13, 135.95, 136.21, 142.56; HRMS (ESI) C$_{27}$H$_{32}$O$_3$SiK: 471.2128, (M+K)$^+$: 471.1759.

Preparation of [(2R,3S,4S)-4-(tert-Butyldiphenylsilyloxy)-2,3-(O-isopropylidenedioxy)-1-cyclopentene]ethanol (Compound 14)

As per chemical scheme II (FIG. 2), after dissolving (2R,3S,4S)-4-(tert-Butyldiphenylsilyloxy)-1-ethenyl-2,3-(O-isopropylidenedioxy)-1-cyclopentene (Compound 13) (5 g, 12.37 mmol) in THF (20 mL), 9-BBN (38 mL, 0.5 M, 18.56 mmol in THF) was added at 0° C. and the above solution was stirred for 4 hours at room temperature. After adding water (50mL) and NaBO$_3$.4H$_2$O (2.47 g, 24.7 mmol) to the reaction mixture, it was stirred for 15 hours at room temperature and filtered. Filtrate was extracted with ethyl acetate, and the above organic layer was dehydrated by adding anhydrous MgSO$_4$ after washing with brine. [(2R,3S,4S)-4-(tert-Butyldiphenylsilyloxy)-2,3-(O-isopropylidenedioxy)-1-cyclopentene]ethanol (Compound 14) (4.2 g, 78%) was obtained in the form of colorless oil by separating the residue, obtained through distillation of the resultant under reduced pressure after filtering the above solution, with silica gel column (EtOAc:hexane=2:1).

$[\alpha]^{19.2}_D$ +31.61° ($c$ 11.8, CH$_2$Cl$_2$); $^1$H NMR (400 MHz, CD$_3$OD) d 1.06 (s, 9H), 1.34 (s, 3H), 1.45 (s, 3H), 2.32-2.38 (m, 2H), 3.64-3.68 (m, 2H), 4.40 (t, J=5.6 Hz, 1H), 4.70 (d, J=5.6 Hz, 1H), 5.44 (s, 1H), 7.36-7.46 (m, 6H), 7.71-7.74 (m, 2H), 7.77-7.80 (m, 2H); $^{13}$C (100 MHz, CD$_3$OD) d 20.16, 27.18, 27.43, 28.11, 32.49, 61.10, 76.58, 80.13, 85.74, 112.97, 128.65, 128.74, 130.89, 130.93, 131.60, 135.20, 135.39, 136.90, 137.12, 143.66; HRMS (ESI) C$_{27}$H$_{32}$O$_3$SiK: 471.2128, (M+K)$^+$471.1759.

Preparation of (2,2-Dimethyl-propionic acid 2-[(2R,3S,4S)-4-(tert-butyldiphenylsilanyloxy)-2,3-(O-isopropylidenedioxy)-cyclopent-1(5)-enyl]-ethyl ester (Compound 15)

As per chemical scheme II (FIG. 2), after dissolving [(2R,3S,4S)-4-(tert-Butyldiphenylsilyloxy)-2,3-(O-isopropylidenedioxy)-1-cyclopentene]ethanol (4.0 gm, 9.13 mmol) in CH$_2$Cl$_2$ (50 mL), DMAP (0.12 gm, 0.91 mmol) and N,N-diisopropylethylamine (5.75 mL, 27.39 mmol) were added at 0° C. in the presence of nitrogen and stirred for 10 minutes. Trimethylacetyl chloride (1.7 mL, 13.69 mmol) was added slowly to the above solution and stirred for 10 hours at room temperature. The reaction mixture was extracted with CH$_2$Cl$_2$ after adding aqueous NH$_4$Cl solution. The above organic layer was dehydrated by adding MgSO$_4$ after washing with brine. 2,2-Dimethyl-propionic acid 2-[(2R,3S,4S)-4-(tert-butyldiphenylsilanyloxy)-2,3-(O-isopropylidenedioxy)-cyclopent-1(5)-enyl]-ethyl ester (Compound 15) (4.4 g, 93%) was obtained in the form of anhydrous oil by separating the residue, obtained through distillation of the resultant under reduced pressure after filtering the above solution, with silica gel column (EtOAc:hexane=3:1).

$[\alpha]^{19.9}_D$ −5.21° (c 71.0, CH$_2$Cl$_2$); $^1$H NMR (400 MHz, CDCl$_3$) d 1.09 (s, 9H), 1.15 (s, 9H), 1.38 (s, 3H), 1.48 (s, 3H), 2.39-2.57 (m, 2H), 4.12-4.18 (m, 1H), 4.23-4.29 (m, 1H), 4.40 (t, J=5.6 Hz, 1H), 4.51-4.54 (m, 1H), 4.68 (d, J=5.6 Hz, 1H), 5.44 (s, 1H), 7.36-7.46 (m, 6H), 7.71-7.75 (m, 2H), 7.78-7.82 (m, 2H); $^{13}$C (100 MHz, CDCl$_3$) d 19.48, 26.99, 27.33, 27.82, 27.88, 38.84, 62.12, 75.26, 78.84, 84.70, 112.09, 127.66, 127.77, 129.80, 131.12, 134.16, 134.40, 135.86, 136.15, 141.42, 178.54; HRMS (ESI) C$_{31}$H$_{42}$O$_5$Na: 545.2802, (M+Na)$^+$: 545.2703.

Preparation of 2,2-Dimethyl-propionic acid 2-[(3S,4S,5R)-4,5-(O-isopropylidenedioxy)-cyclopent-3-ol]-ethyl ester (Compound 16)

As per chemical scheme II (FIG. 2), after dissolving 2,2-Dimethyl-propionic acid 2-[(2R,3S,4S)-4-(tert-butyldiphenylsilanyloxy)-2,3-(O-isopropylidenedioxy)-cyclopent-1(5)-enyl]-ethyl ester (Compound 15) (4.2 g, 8.04 mmol) in THF (120 mL), tetra-butyl-n-ammonium fluoride (12.0 mL in THF,1M solution, 12.0 mmol) was added at 0° C. and stirred for 2 hours at room temperature. 2,2-Dimethyl-propionic acid 2-[(3S,4S,5R)-4,5-(O-isopropylidenedioxy)-cyclopent-3-ol]-ethyl ester (Compound 16) (2.2 g, 96%) was obtained in the form of colorless liquid by separating the residue, obtained through distillation of the reaction mixture under reduced pressure, with silica gel column (EtOAc:hexane=3:2).

$[\alpha]^{19.6}_D$ +2.32° (c 11.6, CH$_2$Cl$_2$); $^1$H NMR (400 MHz, CDCl$_3$) d 1.17 (s, 9H), 1.39 (s, 3H), 1.41 (s, 3H), 2.43-2.56 (m, 2H), 2.65 (d, J=9.2 Hz, 1H), 4.15-4.20 (m, 1H), 4.24-4.32 (m, 1H), 4.55 (m, 1H), 4.73 (pseudo t, J=5.6 Hz, 1H), 4.88 (d, J=5.6 Hz, 1H), 5.55 (s, 1H); $^{13}$C (100 MHz, CDCl$_3$) d 26.93, 27.38, 27.74, 27.87, 38.93, 62.06, 73.61, 77.84, 84.84, 112.63, 131.36, 142.12, 178.61; HRMS (ESI) C$_{15}$H$_{24}$O$_5$ Na: 307.1621, (M+Na)$^+$: 307.1514.

Preparation of 2,2-Dimethyl-propionic acid 2-[(1R,2R,3R,4R,5S) 4,5-(O-isopropylidenedioxy)-1(2)oxirane-cyclopent-3-ol]-ethyl ester (Compound 17a) and 2,2-Dimethyl-propionic acid 2-[(1S,2S,3R,4R,5S)-4,5-(O-isopropylidenedioxy)-1(2)oxirane-cyclopent-3-ol]-ethyl ester (Compound 17b)

As per chemical scheme II (FIG. 2), after adding the solution resulted from dissolving m-CPBA (3 g, 15.48 mmol) in anhydrous CH$_2$Cl$_2$ (50 mL) to the solution resulted from dissolving 2,2-Dimethyl-propionic acid 2-[(3S,4S,5R)-4,5-(O-isopropylidenedioxy)-cyclopent-3-ol]-ethyl ester (Compound 16) (2.2 g, 7.74 mmol) in anhydrous CH$_2$Cl$_2$ (50 mL) at −40° C., it was stirred for 2 days at room temperature. After completion of the reaction, aqueous NH$_4$Cl solution was added to the reaction mixture, which was then extracted with ethyl acetate. The organic layer was dehydrated by adding anhydrous MgSO$_4$ after washing with aqueous NaHSO$_3$ solution and brine. 2,2-Dimethyl-propionic acid 2-[(1R,2R,3R,4R,5S) 4,5-(O-isopropylidenedioxy)-1(2)oxirane-cyclopent-3-ol]-ethyl ester (Compound 17a) (1.65 g, 71%) and 2,2-Dimethyl-propionic acid 2-[(1S,2S,3R,4R,5S)-4,5-(O-isopropylidenedioxy)-1(2)oxirane-cyclopent-3-ol]-ethyl ester (Compound 17b) (0.2 g, 8.6%) were obtained in the form of solid and anhydrous oil, respectively, by separating the residue, obtained through the distillation of the filtered solution under reduced pressure, with silica gel column (EtOAc:hexane=3:1 to 2:1).

Compound 17a: $[\alpha]^{18.7}_D$ +2.88° (c 9.0, CH$_2$Cl$_2$); $^1$H NMR (400 MHz, CDCl$_3$) d 1.18 (s, 9H), 1.30 (s, 3H), 1.55 (s, 3H), 2.03-2.17 (m, 2H), 2.78 (bs, 1H), 3.47 (dd, J$_1$=1.6, J$_2$=1.2 Hz, 1H), 4.05 (ddd, J$_1$=12.0, J$_2$=6.4, J$_3$=5.6 Hz, 1H), 4.15 (d, J=4.8 Hz, 1H), 4.32 (ddd, J$_1$=13.2, J$_2$=7.6, J$_3$=5.6 Hz, 1H), 4.52 (dt, =6.4, J$_2$=1.2 Hz, 1H), 4.62 (d, J=6.8 Hz, 1H); $^{13}$C (100 MHz, CDCl$_3$) d 26.12, 26.56, 27.35, 29.68, 38.86, 60.36, 64.78, 64.78, 67.0, 70.11, 77.55, 80.50, 114.63, 178.63; HRMS (ESI) C$_{15}$H$_{25}$O$_6$: 301.157, (M+H)$^+$: 301.1643.

Compound 17b: $[\alpha]^{19.8}_D$ −7.13° (c 92.0, CH$_2$Cl$_2$); $^1$H NMR (400 MHz, CDCl$_3$) d 1.20 (s, 9H), 1.37 (s, 3H), 1.51 (s, 3H), 2.03 (dt, J$_1$=15.2, J$_2$=6.4 Hz, 1H), 2.35 (dt, J$_1$=15.2, J$_2$=6.4 Hz, 1H), 2.84 (bs, 1H), 3.49 (s, 1H), 4.07 (d, J=6.0 Hz, 1H), 4.21 (t, J=12.4 Hz, 2H), 4.50 (td, J$_1$=6.0, J$_2$=0.8 Hz, 1H), 4.62 (dd, J$_1$=5.6, J$_2$=1.2 Hz, 1H).; $^{13}$C (100 MHz, CDCl$_3$) d 24.66, 26.31, 27.24, 27.53, 60.37, 65.83, 66.41, 68.60, 80.11, 81.12, 113.21, 178.41; HRMS (ESI) $C_{15}H_{25}O_6$: 301.1571, $(M+H)^+$: 301.1643.

Preparation of 2,2-Dimethyl-propionic acid 2-[(1R,2S,3R,4R,5S)-2-fluoro-4,5-(O-isopropylidenedioxy)-cyclopent-1,3-diol]-ethyl ester (Compound 18a)

As per chemical scheme II (FIG. 2), after adding $KHF_2$ (1.0 g, 6.40 mmol) and tetra n-butyl-ammonium dihydrogentrifluoride (2.0 g, 6.6 mmol) to the solution resulted from dissolving 2,2-Dimethyl-propionic acid 2-[(1R,2R,3R,4R,5S)4,5-(O-isopropylidenedioxy)-1(2)oxirane-cyclopent-3-ol]-ethyl ester (Compound 17a) (1.1 g, 3.66 mmol) in anhydrous DMF (5 mL), the reaction mixture has been heated at 130° C. in the glass double-layer tube for 3 days. After the completion of the reaction, water was added to the reaction mixture, which was then extracted with ethyl acetate. This organic layer was dehydrated by adding anhydrous $MgSO_4$ after washing with brine. 2,2-Dimethyl-propionic acid 2-[(1R,2S,3R,4R,5S)-2-fluoro-4,5-(O-isopropylidenedioxy)-cyclopent-1,3-diol]-ethyl ester (Compound 18a) (0.9 g, 77%) was obtained in the form of sticky oil by separating the residue, obtained through distillation of the filtered solution under reduced pressure, with silica gel column (EtOAc:hexane=2:1 to 2:1).

$[\alpha]^{20.1}_D$ –21.36° (c 24.1, $CH_2Cl_2$); $^1H$ NMR (400 MHz, $CDCl_3$) d 1.18 (s, 9H), 1.37 (s, 3H), 1.54 (s, 3H), 1.57-1.64 (m, 1H), 2.11-2.19 (m, 1H), 3.0 (bs, 1H), 3.46 (s, 1H), 4.04 (td, $J_1$=14.4, $J_2$=5.6 Hz, 1H), 4.20-4.26 (m, 1H), 4.30-4.37 (m, 1H), 4.48 (dd, $J_1$=6.4, $J_2$=2.4 Hz, 1H), 4.64 (dt, $J_1$=6.4, $J_2$=2.0 Hz, 1H), 4.65 (dd, $J_1$=51.2, $J_2$=5.6 Hz, 1H); $^{13}C$ (100 MHz, $CDCl_3$): d 24.52, 26.01, 27.32, 31.79, 38.83, 60.14, 71.0 (d, $J_{C-F}$=24.4 Hz), 75.61(d,$J_{C-F}$=19.9 Hz), 76.60 (d,$J_{C-F}$=6.1 Hz), 81.02, 102.0 (d, $J_{C-F}$=188.4 Hz), 113.52, 178.69; $^{19}F$ (376 MHz, $CDCl_3$) d-208.70; HRMS (ESI) $C_{15}H_{25}FO_6Na$: 343.1639, $(M+Na)^+$: 343.1639.

Preparation of 2,2-Dimethyl-propionic acid 2-[(1S,2R,3R,4R,5S)-2-fluoro-4,5-(O-isopropylidenedioxy)-cyclopent-1,3-diol]-ethyl ester (Compound 18b)

As per chemical scheme II (FIG. 2), after adding $KHF_2$ (0.6 g, 3.23 mmol) and tetrabutylammonium dihydrogentrifluoride (1.29 g, 4.31 mmol) to the solution resulted from dissolving 2,2-Dimethyl-propionic acid 2-[(1R,2R,3R,4R,5S)-4,5-(O-isopropylidenedioxy)-1(2)oxirane-cyclopent-3-ol]-ethyl ester (Compound 17a) (0.647 g, 2.15 mmol) in anhydrous DMF (5 mL), the reaction mixture has been heated at 150° C. in the double-layer tube for 4 days. After the completion of the reaction, water was added to reaction mixture, which was then extracted with ethyl acetate. This organic layer was dehydrated by adding anhydrous $MgSO_4$ after washing with brine. 2,2-Dimethyl-propionic acid 2-[(1S,2R,3R,4R,5S)-2-fluoro-4,5-(O-isopropylidenedioxy)-cyclopent-1,3-diol]-ethyl ester (Compound 18b) (0.33 g,48%) was obtained in the form of sticky oil by separating the residue, obtained through distillation of the filtered solution under reduced pressure with silica gel column (EtOAc:hexane=3:1).

$[\alpha]^{19.5}_D$ +6.94° (c 5.9, $CH_2Cl_2$); $^1H$ NMR (400 MHz, $CDCl_3$) d 1.20 (s, 9H), 1.31 (s, 3H), 1.44 (s, 3H), 2.18-2.22 (m, 2H), 2.79 (bd, J=11.2 Hz, 1H), 2.95 (bs, 1H), 4.27-4.31 (m, 1.5H and half part of proton connected to F) 4.34-4.40 (m, 3H), 4.48-4.49 (m, 0.5 proton), 4.70 (td, $J_1$=6.0, $J_2$=0.8 Hz, 1H); $^{13}C$ (100 MHz, $CDCl_3$) d 24.48, 25.98, 27.34, 30.19, 38.94, 61.83, 72.05 (d, $J_{C-F}$=16.1 Hz), 78.72 (d,$J_{C-F}$=19.9 Hz), 78.89 (d,$J_{C-F}$=19.8 Hz), 85.30, 96.88 (d, $J_{C-F}$=188.9 Hz), 112.34, 179.19; $^{19}F$ (376 MHz, $CDCl_3$) d-210.81; HRMS (ESI) $C_{15}H_{25}FO_6Na$: 343.1639, $(M+Na)^+$: 343.1522.

Preparation of 2,2-Dimethyl-propionic acid 2-[(4R,5S)-2-fluoro-4,5-(O-isopropylidenedioxy)-3-oxocyclopent-1(2)-en]-ethyl ester (Compound 19) from 2,2-Dimethyl-propionic acid 2-[(1R,2S,3R,4R,5S)-2-fluoro-4,5-(O-isopropylidenedioxy)-cyclopent-1,3-diol]-ethyl ester (Compound 18a)

As per chemical scheme II (FIG. 2), EDCl (1.0 g, 5.015 mmol) was added to the solution resulted from dissolving 2,2-Dimethyl-propionic acid 2-[(1R,2S,3R,4R,5S)-2-fluoro-4,5-(O-isopropylidenedioxy)-cyclopent-1,3-diol]-ethyl ester (Compound 18a) (535 mg, 1.671 mmol) in anhydrous DMSO (4mL) and benzene (8mL) in the presence of nitrogen current. After adding pyridine (0.2 mL, 2.50 mmol) and TFA (0.19 mL, 1.67 mmol) to this solution, it was stirred at room temperature for 1 day. After the completion of the reaction, water was added to reaction mixture, which was then extracted with ethyl acetate. The above organic layer was dehydrated by adding anhydrous $MgSO_4$ after washing with brine. 2,2-Dimethyl-propionic acid 2-[(4R,5S)-2-fluoro-4,5-(O-isopropylidenedioxy)-3-oxocyclopent-1(2)-en]-ethyl ester (Compound 19) (300 mg, 60%) was obtained in the form of solid by separating the residue, obtained through distillation of the resultant under reduced pressure after filtering the above solution, with silica gel column (EtOAc:hexane=3:1).

$[\alpha]^{19.9}_D$ –13.57° (c 5.6, $CH_2Cl_2$); $^1H$ NMR (400 MHz, $CDCl_3$) d 1.17 (s, 9H), 1.40 (s, 6H), 2.76-2.91 (m, 2H), 4.25-4.31 (m, 1H), 4.42-4.48 (m, 1H), 4.52 (dd, $J_1$=5.6, $J_2$=2.8 Hz, 1H), 5.17 (pseudo t, J=5.6 Hz, 1H); $^{13}C$ (100 MHz, $CDCl_3$) d 26.27, 27.29, 27.78, 38.93, 60.37, 75.0 (d, $J_{C-F}$=6.6 Hz), 75.38 (d, $J_{C-F}$=7.3 Hz), 115.78, 146.38, 155.0 (d, $J_{C-F}$=287.8 Hz), 178.52, 191.83, 192.0; $^{19}F$ (376 MHz, $CDCl_3$) d-140.40; HRMS (ESI) calculated for $C_{15}H_{21}FO_5Na$: 323.137, Found $(M+Na)^+$: 323.1262.

Preparation of 2,2-Dimethyl-propionic acid 2-[(4R,5S)-2-fluoro-4,5-(O-isopropylidenedioxy)-3-oxocyclopent-1(2)-en]-ethyl ester (Compound 19) from 2,2-Dimethyl-propionic acid 2-[(1S,2R,3R,4R,5S)-2-fluoro-4,5-(O-isopropylidenedioxy)-cyclopent-1,3-diol]-ethyl ester (Compound 18b)

As per chemical scheme II (FIG. 2), EDCl (1.0 g, 5.015 mmol) was added to the solution resulted from dissolving 2,2-Dimethyl-propionic acid 2-[(1S,2R,3R,4R,5S)-2-fluoro-4,5-(O-isopropylidenedioxy)-cyclopent-1,3-diol]-ethyl ester (Compound 18b) (330 mg, 1.03 mmol) in anhydrous DMSO (6 mL) and benzene (8mL) in the presence of nitrogen. After adding pyridine (0.25 mL, 3.09 mmol) and TFA (0.15 mL, 1.54 mmol) to the above solution, it was stirred at room temperature for 1 day. After the completion of the reaction, water was added to reaction mixture, which was then extracted with ethyl acetate. This organic layer was dehydrated by adding anhydrous $MgSO_4$ after washing with brine. 2,2-Dimethyl-propionic acid 2-[(4R,5S)-2-fluoro-4,5-(O-isopropylidenedioxy)-3-oxocyclopent-1(2)-en]-ethyl ester (Compound 19) (300 mg, 60%) was obtained in the form of solid by separating the residue, obtained through distillation of the resultant under reduced pressure after filtering the above solution with silica gel column (EtOAc:hexane=2:1).

Preparation of 2,2-Dimethyl-propionic acid 2-[(3S,4R,5S)-2-fluoro-4,5-(O-isopropylidenedioxy)-3-ol cyclopent-1(2)-en]-ethyl ester (Compound 3)

As per chemical scheme II (FIG. 2), after adding $CeCl_3.7H_2O$ (447 mg, 1.2 mmol) to the solution resulted from dissolving 2,2-Dimethyl-propionic acid 2-[(4R,5S)-2-fluoro-4,5-(O-isopropylidenedioxy)-3-oxocyclopent-1(2)-en]-ethyl ester (Compound 19) (300 mg, 1 mmol) in MeOH (50 mL), it was stirred for five minutes. After adding $NaBH_4$ (30 mg, 0.75 mmol) to this solution at 0° C., it was stirred for 1 hour. After the completion of the reaction, water was added to reaction mixture, which was then extracted with ethyl acetate. The above organic layer was dehydrated by adding anhydrous $MgSO_4$ after washing with brine. 2,2-Dimethyl-propionic acid 2-[(3S,4R,5S)-2-fluoro-4,5-(O-isopropylidenedioxy)-3-oxocyclopent-1(2)-en]-ethyl ester (Compound 3) (267 mg, 91%) was obtained in the form of colorless oil by separating the residue, obtained through distillation of the resultant under reduced pressure after filtering the above solution, with silica gel column (EtOAc:hexane=2:1).

$[a]^{19.8}_D$ +2.60° (c 9.2, $CH_2Cl_2$); $^1H$ NMR (400 MHz, $CDCl_3$) d 1.17 (s, 9H), 1.39 (s, 3H), 1.44 (s, 3H), 2.41-2.59 (m, 2H), 2.77 (d, J=9.2 Hz, 1H), 4.09-4.17 (m, 1H), 4.26-4.32 (m, 1H), 4.40-4.45 (m, 1H), 4.69 (dt, $J_1$=6.0, $J_2$=3.6 Hz, 1H), 4.91 (pseudo t, J=6.4 Hz, 1H); $^{13}C$ (100 MHz, $CDCl_3$) d 23.65, 26.61, 27.34, 27.81, 61.46, 69.0 (d, $J_{C-F}$=20.5 Hz), 74.04(d, $J_{C-F}$=8.0 Hz), 80.0 (d, $J_{C-F}$=9.5 Hz), 112.64, 114.63 (d, $J_{C-F}$=6.6 Hz), 158.0 (d, $J_{C-F}$=284.9 Hz), 178.59; $^{19}F$ (376 MHz, $CDCl_3$) d-132.69; HRMS (ESI) $C_{15}H_{23}FO_5Na$: 325.1528, $(M+Na)^+$: 325.1528.

EXAMPLE 3

Preparation of 2,2-Dimethyl-propionic acid 2-[(2R,3S,4S)-4-(6-chloro-purine-9-yl)-5-fluoro-2,3-dihydroxy cyclopent-1(5)-en]-ethyl ester (Compound 6 where X is Cl and $R_2$ is H)

As per chemical scheme III (FIG. 3), after adding the solution resulted from dissolving DIAD (0.4 ml, 1.90 mmol) in anhydrous TFH (10 mL) to the solution resulted from dissolving 2,2-Dimethyl-propionic acid 2-[(3S,4R,5S)-2-fluoro-4,5-(O-isopropylidenedioxy)-3-ol-cyclopent-1(2)-en]-ethyl ester (Compound 3) (230 mg, 0.76 mmol), $PPh_3$ (0.5 g, 1.90 mmol) and 6-chloro-purine (Compound 4 where X is Cl and $R_2$ is H) (294 mg, 1.90 mmol) in the anhydrous TFH (30 mL) at 0° C., it was stirred for 15 minutes. 2,2-Dimethyl-propionic acid 2-[(2R,3S,4S)-4-(6-chloro-purine-9-yl)-5-fluoro-2,3-(O-(O-Isopropylidenedioxy))-1(5)-en]-ethyl ester (Compound 5 where X is Cl and $R_2$ is H) (300 mg mixture with DIAD by-product) was obtained in the form of while bubble-type solid by separating the residue, obtained through enrichment of the reaction mixture under reduced pressure, with silica gel column (EtOAc:hexane=2:1). Compound 5 (X is Cl and $R_2$ is H): $^1H$ NMR (400 MHz, mixture with $CDCl_3$ DIAD by-product)

After adding 2NHCl (5 mL) to the solution resulted from dissolving 2,2-Dimethyl-propionic acid 2-[(2R,3S,4S)-4-(6-chloro-purine-9-yl)-5-fluoro-2,3-(O-(O-Isopropylidenedioxy))-1(5)-en]ethyl ester (Compound 5 where X is Cl and $R_2$ is H) in TFH (10 mL) at 0° C., it was stirred at 45° C. for 1 day. After the completion of the reaction, the solution was neutralized with 1N NaOH and extracted with ethyl acetate. This organic layer was dehydrated by adding anhydrous $MgSO_4$ after washing with brine. 2,2-Dimethyl-propionic acid 2-[(2R, 3S,4S)-4-(6-chloro-purine-9-yl)-5-fluoro-2,3-dihydroxycyclopent-1(5)-en]ethyl ester (Compound 6 where X is Cl and $R_2$ is H) (yield over two steps 150 mg, 49.6%) was obtained in the form of colorless solid by separating the residue, obtained through distillation of the resultant under reduced pressure after filtering the above solution, with silica gel column ($CH_2Cl_2$:MeOH=20:1).

Compound 6 (X is Cl and $R_2$ is H): mp: 153-154° C. $[a]^{19.4}_D$-72.28° (c 5.7, $CH_2Cl_2$). UV (MeOH) $\lambda_{max}$ 261.0 nm; $^1H$ NMR (400 MHz, MeOH-D4) d 1.16 (s, 9H), 2.53-2.60 (m, 1H), 2.63-2.71 (m, 1H), 4.25-4.35 (m, 2H), 4.64-4.70 (m, 1H), 4.80 (pseudo t, J=4.4 Hz, 1H), 5.66-5.69 (m, 1H), 8.59 (s, 1H), 8.71 (s, 1H); $^{13}C$ (100 MHz, $CDCl_3$) d 24.91, 27.53, 39.78, 62.79, 64.53(d, $J_{C-F}$=19.1Hz), 73.0 (d, $J_{C-F}$=9.2Hz), 74.82, 126.76 (d, $J_{C-F}$=122.38 Hz), 147.58, 151.66, 153.15, 155.84, 160.2, 180.10; $^{19}F$ (376 MHz, $CDCl_3$) d-314.85; HRMS (ESI) $C_{17}H_{21}ClFN_4O_4$: 399.116, $(M+H)^+$: 399.1232.

Preparation of (1S,2R,5S)-5-(6-Aminopurine-9-yl)-4-fluoro-3-hydroxyethyl-cyclopent-3(4)-en-1,2-diol (Compound 1 where X is $NH_2$ and $R_2$ is H)

As per chemical scheme III (FIG. 3), after dissolving 2,2-Dimethyl-propionic acid 2-[(2R,3S,4S)-4-(6-chloro-purine-9-yl)-5-fluoro-2,3-dihydroxycyclopent-1(5)-en]-ethyl ester (Compound 6 where X is Cl and $R_2$ is H) in saturated solution of ammonia t-BuOH (10 mL), it was heated at 120° C. in steel bomb for 1 day. Adenine derivative (135 mg, 95%) was obtained in the form of white solid by separating the residue, obtained through distillation of the reaction mixture under reduced pressure, with silica gel column ($CH_2Cl_2$:MeOH=20:1).

NaOMe (150 mg) was added to the solution resulted from dissolving the above resultant adenine derivative (135 mg) in anhydrous MeOH (3 mL) and was heated at 45° C. for 3 hours. After the completion of the reaction, (1S,2R,5S)-5-(6-Aminopurine-9-yl)-4-fluoro-3-hydroxyethyl-cyclopent-3(4)-en-1,2-diol (Formula 1 where X is $NH_2$ and $R_2$ is H) (60 mg,55%) was obtained in the form of colorless solid by separating the residue, obtained through distillation of the resultant under reduced pressure after neutralizing the solution with acetic acid, with silica gel column ($CH_2Cl_2$:MeOH=4:1).

mp: 186-187° C. $[a]^{27.2}_D$-124.9° (c 5.5, MeOH); UV (MeOH) $\lambda_{max}$ 258.0 nm; $^1H$ NMR (400 MHz, MeOH-D4) d 2.48-2.54 (m, 2H), 3.76-3.81 (m, 2H), 4.51 (td, $J_1$=5.6, $J_2$=1.6 Hz, 1H), 4.69 (pseudo t, J=4.4 Hz, 1H), 5.53-5.56 (m, 1H), 8.17 (s, 1H), 8.18 (s, 1H); $^{13}C$ (100 MHz, MeOH-D4) d 28.66, 60.39, 63.6 (d, J=18.3 Hz), 72.5 (d, J=9.6 Hz), 75.59 (d, J=18.3 Hz), 120.58, 121.24 (d, J=3.6 Hz), 141.78, 150.92, 153.58, 153.92, 157.0 (d, J=108.4 Hz); $^{19}F$(376 MHz, MeOH-D4) d-135.0; HRMS (ESI) $C_{12}H_{14}FNO_3$: 295.1071, $(M+H)^+$: 296.1151.

EXAMPLE 4

Preparation of 2,2-Dimethyl-propionic acid 2-[(2R,3S,4S)-4-(3-benzoyal-uracil-1-yl)-5-fluoro-2,3-dihydroxy cyclopent-1(5)-en]-ethyl ester (Compound 9)

As per chemical scheme IV (FIG. 4), after adding the solution resulted from dissolving DIAD (0.7 ml, 3.47 mmol) in anhydrous THF (10 mL) to the solution resulted from dissolving 2,2-Dimethyl-propionic acid 2-[(3S,4R,5S)-2-fluoro-4,5-(O-isopropylidenedioxy)-3-ol cyclopent-1(2)-en]-ethyl ester (Compound 3) (420 mg, 1.39 mmol), $PPh_3$ (0.911 g, 3.47 mmol) and 3-N-benzoyluracil (3-Bz-uracil; Compound 7) (0.75 g, 3.47 mmol) in anhydrous THF (30 mL) at 0° C., it was stirred at room temperature for 24 hours. The intermediate (Compound 8) (610 mg mixture with DIAD by-product) was obtained in the form of white bubble-type solid by separating the residue, obtained through enrichment of the reaction mixture under reduced pressure, with silica gel column (EtOAc:hexane=2:1).

Compound 8: 1H NMR (mixture with DIAD by-product 400 MHz, $CDCl_3$): 1.16 (s, 9H), 1.33 (s, 3H), 1.43 (s, 3H), 1.35-1.42 (m, 1H), 1.66-1.76 (m, 1H), 2.50-2.67 (m, 1H), 3.76 (pseudo t, J=7.2 Hz, 1H), 4.17-4.38 (m, 1H), 4.65-4.41 (dd, $J_1$=6.0, $J_2$=4.4 Hz, 1H), 4.80 (pseudo t, J=5.6 Hz, 1 h), 5.45 (dt,$J_1$=6.4, $J_2$=2.0 Hz, 1H), 5.56 (s, 1H), 8.09 (s, 1H), 8.75 (s, 1H). $^{19}F$ (376 MHz, $CDCl_3$): −135.02.

After adding 2N HCl (5 mL) to the solution resulted from dissolving the intermediate (Compound 8) (610 mg mixture with DIAD by-product) in anhydrous TFH (10 mL) at 0° C., it was heated at 45° C. for 1 day. After the completion of the reaction, the solution was neutralized with 1N NaOH and extracted with ethyl acetate. This organic layer was dehydrated by adding anhydrous MgSO$_4$ after washing with brine. 2,2-Dimethyl-propionic acid 2-[(2R,3S,4S)-4-(3-benzoyl-uracil-1-yl)-5-fluoro-2,3-dihydroxycyclopent-1(5)-en]-ethyl ester (Compound 9) (yield over two steps 380 mg, 60%) was obtained in the form of bubble-type solid by separating the residue, obtained through distillation of the resultant under reduced pressure after filtering the above solution, with silica gel column (CH$_2$Cl$_2$:MeOH=20:1).

Compound 9: mp: 229-230° C. [a]$^{20.0}_D$ 18.11° (c 5.3, CH$_2$Cl$_2$). UV (MeOH) $\lambda_{max}$ 255.0 nm. $^1$H NMR (400 MHz, MeOH-D$_4$) d 1.14 (s, 9H), 2.47-2.52 (m, 1H), 2.57-2.64 (m, 1H), 4.19-4.29 (m, 3H), 4.80 (td, J$_1$=6.0, J$_2$=1.6 Hz, 1H), 5.36 (bs, 1H), 5.89 (d, J=8 Hz, 1H), 7.55-7.61 (m, 3H), 7.71-7.75 (m, 1H), 7.93-7.96 (m, 2H). $^{13}$C (100 MHz, CDCl$_3$): d 24.95, 27.54, 39.76, 62.79, 62.73, 66.82 (d, J$_{C-F}$=18.3 Hz), 72.73 (d, J$_{C-F}$=9.9 Hz), 74.20 (d, J$_{C-F}$=5.4 Hz), 103.16, 128.0 (d, J$_{C-F}$=104.5 Hz), 130.49, 131.48, 136.45, 144.63, 151.29, 153.22, 156.03, 169.97, 180.19. $^{19}$F (376 MHz, CDCl$_3$): d -134.481. HRMS, (ESI) C$_{23}$H$_{25}$FN$_2$O$_7$Na: 483.1642, (M+Na)$^+$: 483.1534.

Preparation of (1S,2R,5S)-4-Fluoro-3-hydroxyethyl-5-(uracil-1-yl)-cyclopent-3(4)-en-1,2-diol (Compound 10)

As per chemical scheme IV (FIG. 4), after dissolving 2,2-Dimethyl-propionic acid 2-[(2R, 3S,4S)-4-(3-benzoyl-uracil-1-yl)-5-fluoro-2, 3-dihydroxycyclopent-1(5)-en]-ethyl ester (Compound 9) (380 mg, 1.21 mmol) in anhydrous MeOH (5 mL), NaOMe (500 mg) was added and it was heated at 45° C. for 3 hours. After the completion of the reaction, (1S,2R,5S)-4-Fluoro-3-hydroxyethyl-5-(uracil-1-yl)-cyclopent-3(4)-en-1,2-diol (Compound 10) (120 mg, 53%) was obtained in the form of bubble-type solid by separating the residue, obtained from evaporating the solvent following neutralizing the solution with glacial acetic acid, with silica gel column (CH$_2$Cl$_2$:MeOH=20:1).

Mp: 166-167° C. [a]$^{20.4}_D$ -103.71° (c 7.8, MeOH). UV (MeOH) $\lambda_{max}$ 264.0 nm.$^1$H NMR (400 MHz, MeOH-D$_4$): d 2.41-2.52 (m, 2H), 3.68-3.79 (m, 2H), 4.16 (td, J$_1$=6.0, J$_2$=1.6 Hz, 1H), 4.55 (td, J$_1$=6.4, J$_2$=1.6 Hz, 1H) 5.44-5.47 (m, 1H), 5.72 (d, J=7.6 Hz, 1H), 7.49 (dd, J$_1$=8, J$_2$=1.2 Hz, 1H) $^{13}$C (100 MHz, MeOH-D4): d 28.58, 60.24, 65.10 (d, J$_{C-F}$=18.3 Hz), 72.70 (d, J$_{C-F}$=9.5 Hz), 74.86, 103.27, 121.90, 143.73, 153.2 (d, J$_{C-F}$=57.5 Hz), 156.29, 166.14. $^{19}$F (376 MHz, MeOH-D$_4$): d-134.96. HRMS, (ESI) C$_{11}$H$_{13}$FN$_2$O$_5$Na: 295.0808, (M+Na)$^+$295.07.

EXAMPLE 5

Preparation of (1S,2R,5S)-5-(Cytosine-1-yl)-4-fluoro-3-hydroxyethyl-cyclopent-3(4)-en-1,2-diol (Compound 11)

As per chemical scheme V (FIG. 5), after dissolving (1S, 2R,5S)-4-Fluoro-3-hydroxyethyl-5-(uracil-1-yl)-cyclopent-3(4)-en-1,2-diol (Compound 10) (120 mg, 0.441 mmol) in anhydrous pyridine (1 mL), Ac$_2$O (1 mL) was added and it was stirred at room temperature for 15 hours. The triacetate compound (110 mg, 62%) as written in Compound 6 was obtained in the form of oil solid by separating the residue, obtained from evaporating the solvent, with silica gel column (hexane:EtOAc=1:9).

The above resultant triacetate compound was dissolved in anhydrous CH$_3$CN (10 mL), 1,2,4-triazole (drying condition 156 mg, 2.26 mmol) and POCl$_3$ (0.21 mL, 2.26 mmol) were added at 0° C. 15 minutes later, Et$_3$N (0.3 mL) was added. After stirring reaction mixture at 35° C. for 48 hours, Et$_3$N (0.3 mL) and water (1 mL) were added followed by stirring for 10 minutes. After evaporating solvent, the residue was dissolved in 1,4-dioxane, ammonia solution was added, and then it was stirred in the double-layer tube for 10 hours. Afterwards, it was stirred for 24 hours after adding saturated ammonia methanol solution, and (1S,2R,5S)-5-(Cytosine-1-yl)-4-fluoro-3-hydroxyethyl-cyclopent-3(4)-en-1,2-diol (Compound 11) (55 mg, 90% from triacetic acid) was obtained in the form of colorless solid by separating the residue, obtained from evaporating the solvent with reverse phase (using water).

$^1$H NMR (400 MHz, MeOH-D$_4$): d 2.40-2.50 (m, 2H), 3.68-3.79 (m, 2H), 4.17-4.20 (m, 1H), 4.56 (pt, J=4.40 Hz, 1H), 5.41 (bs, 1H), 5.93 (d, J=7.2 Hz, 1H), 7.53 (dd, J$_1$=7.6, J$_2$=0.8 Hz, 1H). HRMS (ESI) C$_{11}$H$_{14}$FN$_3$O$_4$Na: 294.0974, (M+Na)$^+$: 294.0868.

EXAMPLE 6

Measurement of the Growth Inhibition Ability Against Cancer Cells

Step 1) Cancer Cell Preparation

Human cancer cell strains were obtained through the following paths: OVCAR-3 (ovarian cancer), MCF-7 (hormone dependent breast cancer), MDA-MB-231 (breast cancer), HeLa (cervical cancer), PC3 (prostate cancer), LNCap (prostate cancer), HepG2 (liver cancer), A549 (lung cancer), NCI-H226 (lung cancer), Caki-1 (kidney cancer), SK-MEL-28 (melanoma cancer), HT-29 (colorectal cancer), HCT116 (colorectal cancer) and PANC-1 (pancreas cancer) cells were purchased from American Type Culture Collection (ATCC) (Manassas, Va.); U251(brain tumor) cells were purchased from Riken Institutes, Marunouchi, Tokyo, Japan; MKN-45 (gastric cancer) cells were purchased from DSMZ (Germany); and UMRC2 (kidney cancer) cells were purchased from U.S. National Cancer Institute (Bethesda, Md.).

Step 2) Cancer Cell Culture

MDA-MB-231, HCT116, UMRC2, Caki-1 and PANC-1 cells were cultured in Dulbecco's modified Eagle's medium ("DMEM", Invitrogen) including 10% FBS, 100 units/mL penicillin-streptomycin (P/S), 10 mM HEPES and 2 mM L-glutamine. All the other cell strains were cultured in RPMI1640 medium (Invitrogen, Carlsbad, Calif.) including 10% fetal bovine serum (FBS), 1 mM sodium pyruvate, 10 mM HEPES, and 100 units/mL penicillin-streptomycin (P/S). All cells were cultured at 37° C. 5% CO$_2$ humid conditions.

Step 3) Analysis of Cell Growth Inhibition

The cell growth inhibition level of the novel compound synthesized using (1S,2R,5S)-5-(6-Aminopurine-9-yl)-4-fluoro-3-hydroxyethyl-cyclopent-3(4)-en-1,2-diol (compound of Formula 1 where X is NH$_2$ and R$_2$ is H) prepared in the above Example 3, (1S,2R,5S)-4-Fluoro-3-hydroxyethyl-5-(uracil-1-yl)-cyclopent-3(4)-en-1,2-diol (Compound 10) prepared in the above Example 4, (1S,2R,5S)-5-(Cytosine-1-yl)-4-fluoro-3-hydroxyethyl-cyclopent-3(4)-en-1,2-diol (Compound 11) prepared in the above Example 5, Fluoro-neplanocin A, and Homoneplanocin A was analyzed by SRB (sulphorhodamine B) assay according to the publicly known method in the literature.

Human cancer cell strains increased exponentially were divided into the 96-well plates at the density of 2×10$^3$ to 3×10$^3$ cells/well and processed with the compounds of the various concentrations in the present invention on the next day. 0.25% DMSO was used as a control group. Three experiments were performed for each process. The cells were fixed with 10% trichloro-acetic acid at 96 hours after processing with the compound and SRB analysis was carried out. Optical density was measured at 530 nm with Benchmark PlusMicroplate Reader (Bio-Rad Laboratories, Hercules, Calif.). The concentration of the drug to inhibit the cell growth by 50% MICA was measured with Kaledia Graph (Synergy software, Reading, Pa.). The results are shown in Table 1.

TABLE 1

| | HCT-116 (colorectal cancer) | PC-3 (prostate cancer) | T47D (breast cancer) | SNU638 (gastric cancer) | A549 (lung cancer) | K562 (blood cancer) |
|---|---|---|---|---|---|---|
| Compound of Formula 1 ($R_1$ = $NH_2$, $R_2$ = H, Fluoro-homoneplanocin A) | 1.1 | 2.39 | 2.83 | 0.37 | 0.62 | 0.13 |
| Compound 10 | >10 | >10 | >10 | >10 | >10 | >10 |
| Compound 11 | >10 | >10 | >10 | >10 | >10 | >10 |
| Fluoro-neplanocin A | 1.4 | 3.1 | 3.6 | 1.3 | 2.6 | 2.2 |
| Homoneplanocin A | >10 | >10 | >10 | >10 | >10 | >10 |

As shown in the above table, the compound of Formula 1 was found to be able to act as effective anti-cancer drug, exhibiting the effect of cell growth inhibition for colorectal cancer, prostate cancer, breast cancer, gastric cancer, lung cancer and blood cancer.

What is claimed is:

1. A method for treating a cancer in a subject, comprising the step of:
    administering a pharmaceutical composition comprising a fluoro-homoneplanocin A derivative compound of Formula I or a pharmacologically acceptable salt thereof to the subject, thereby treating the cancer,
    wherein the cancer is colorectal cancer, prostate cancer, breast cancer, gastric cancer, lung cancer, or a blood cancer,
    wherein the fluoro-homoneplanocin A derivative compound of Formula I has the chemical structure:

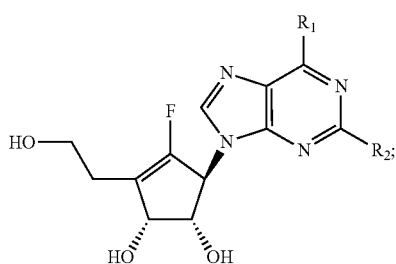

Formula 1 wherein $R_1$ is $NH_2$ or $NH(CH_3)$; and
$R_2$ is H, Cl, Br, or $NH_2$.

2. The method of claim 1, wherein $R_1$ is $NH_2$ and $R_2$ is H.

3. The method of claim 1, wherein the pharmaceutical composition further comprises a pharmaceutically acceptable carrier.

* * * * *